(12) United States Patent
Stumpo et al.

(10) Patent No.: US 12,083,018 B2
(45) Date of Patent: Sep. 10, 2024

(54) HIP ARTHROPLASTY IMPLANTS

(71) Applicant: GLOBUS MEDICAL, INC., Audubon, PA (US)

(72) Inventors: David Stumpo, Collegeville, PA (US); Fred Matthis, South Park, PA (US); Kenny Chen, Philadelphia, PA (US); John M. Loiacono, Collegeville, PA (US); Pasquale Petrera, Salisbury, MD (US); David Morawski, St. Charles, IL (US)

(73) Assignee: Globus Medical, Inc., Audubon, PA (US)

( * ) Notice: Subject to any disclaimer, the term of this patent is extended or adjusted under 35 U.S.C. 154(b) by 950 days.

(21) Appl. No.: 17/111,720

(22) Filed: Dec. 4, 2020

(65) Prior Publication Data

US 2022/0087824 A1 Mar. 24, 2022

Related U.S. Application Data

(63) Continuation-in-part of application No. 17/024,876, filed on Sep. 18, 2020.

(51) Int. Cl.
*A61F 2/34* (2006.01)
*A61F 2/46* (2006.01)
*A61F 2/30* (2006.01)

(52) U.S. Cl.
CPC .............. *A61F 2/34* (2013.01); *A61F 2/4609* (2013.01); *A61F 2002/30112* (2013.01); *A61F 2002/30154* (2013.01); *A61F 2002/30505* (2013.01); *A61F 2002/3417* (2013.01); *A61F 2002/4629* (2013.01); *A61F 2002/4681* (2013.01)

(58) Field of Classification Search
CPC .......... A61F 2/34; A61F 2/4609; A61B 17/56; A61B 17/58; A61B 17/88; A61B 17/8872; A61B 17/92; A61B 17/1746
See application file for complete search history.

(56) References Cited

U.S. PATENT DOCUMENTS

| | | |
|---|---|---|
| 3,698,017 A | 10/1972 | Scales et al. |
| 3,818,512 A | 6/1974 | Shersher |
| 3,863,273 A | 2/1975 | Averill |
| 3,875,593 A | 4/1975 | Shersher |
| 4,172,296 A | 10/1979 | D'Errico |
| 4,650,491 A | 3/1987 | Parchinski |
| 4,666,450 A | 5/1987 | Kenna |
| 4,695,282 A | 9/1987 | Forte et al. |
| 4,704,127 A | 11/1987 | Averill et al. |

(Continued)

*Primary Examiner* — Brian A Dukert

(57) ABSTRACT

An acetabular shell insertion tool with an anti-rotation feature is provided. The insertion tool attaches to an acetabular shell including a center hole having an internal threading and an anti-rotation recess disposed around the center hole and having a predetermined shape. The insertion tool includes an outer shaft and an inner shaft disposed within the outer shaft. The outer shaft has an anti-rotation projection shaped to be received in the anti-rotation recess of the acetabular shell so as to prevent rotation of the outer shaft relative to the acetabular shell, thereby preventing the insertion tool from disengaging from the shell. The inner shaft has a threaded tip adapted to be threaded into the internal threading of the center hole to lock the insertion tool to the acetabular shell.

19 Claims, 15 Drawing Sheets

(56) References Cited

U.S. PATENT DOCUMENTS

| | | | |
|---|---|---|---|
| 4,715,859 A | 12/1987 | Shelkas et al. |
| 4,792,337 A | 12/1988 | Muller |
| 4,795,469 A | 1/1989 | Oh |
| 4,798,610 A | 1/1989 | Averill et al. |
| 4,851,006 A | 7/1989 | Tuke et al. |
| 4,878,916 A | 11/1989 | Rhenter et al. |
| 4,936,861 A | 6/1990 | Muller et al. |
| 4,950,299 A | 8/1990 | Noiles |
| 5,108,446 A | 4/1992 | Wagner et al. |
| 5,108,447 A | 4/1992 | Zeiler et al. |
| 5,116,339 A | 5/1992 | Glock |
| 5,133,764 A | 7/1992 | Poppas et al. |
| 5,156,625 A | 10/1992 | Marchetti et al. |
| 5,222,984 A | 6/1993 | Forte |
| 5,226,917 A | 7/1993 | Schryver |
| 5,376,122 A | 12/1994 | Poppas et al. |
| 5,413,603 A | 5/1995 | Noiles et al. |
| 5,417,696 A | 5/1995 | Kashuba et al. |
| 5,443,519 A | 8/1995 | Averill et al. |
| 5,474,560 A | 12/1995 | Rohr, Jr. |
| 5,507,828 A | 4/1996 | Maumy et al. |
| 5,540,697 A | 7/1996 | Rehmann et al. |
| 5,549,695 A | 8/1996 | Spotorno et al. |
| 5,549,696 A | 8/1996 | Willi |
| 5,571,111 A | 11/1996 | Aboczky |
| 5,584,837 A | 12/1996 | Petersen |
| 5,609,648 A | 3/1997 | Dehy et al. |
| 5,904,688 A | 5/1999 | Gilbert et al. |
| 5,938,702 A | 8/1999 | Lopez et al. |
| 6,042,612 A | 3/2000 | Voydeville |
| 6,059,833 A | 5/2000 | Doets |
| 6,129,765 A | 10/2000 | Lopez et al. |
| 6,152,961 A | 11/2000 | Ostiguy, Jr. et al. |
| 6,162,256 A | 12/2000 | Ostiguy, Jr. et al. |
| 6,334,875 B1 | 1/2002 | Keller |
| 6,379,389 B1 | 4/2002 | Koch |
| 6,425,921 B1 | 7/2002 | Grundei et al. |
| 6,475,243 B1 | 11/2002 | Sheldon et al. |
| 6,626,913 B1 * | 9/2003 | McKinnon ............ A61F 2/367 |
| | | 606/86 R |
| 6,827,742 B2 | 12/2004 | Hayes, Jr. et al. |
| 7,267,693 B1 | 9/2007 | Mandell et al. |
| 7,294,150 B1 | 11/2007 | Mandell et al. |
| RE40,090 E | 2/2008 | Whiteside |
| 7,326,253 B2 | 2/2008 | Snyder et al. |
| 7,335,231 B2 | 2/2008 | McLean |
| 7,455,694 B2 | 11/2008 | Epaules et al. |
| 7,553,332 B2 | 6/2009 | Bacon |
| 7,628,820 B2 | 12/2009 | Grundei et al. |
| 7,708,783 B2 | 5/2010 | Richards |
| 7,749,277 B2 | 7/2010 | McLean |
| 7,766,971 B2 | 8/2010 | Gladdish, Jr. et al. |
| 7,850,738 B2 | 12/2010 | Hayes, Jr. et al. |
| 7,850,938 B2 | 12/2010 | Hayes, Jr. et al. |
| 8,029,571 B2 | 10/2011 | McLean |
| 8,029,572 B2 | 10/2011 | McLean |
| 8,123,815 B2 | 2/2012 | Meridew et al. |
| 8,163,029 B2 | 4/2012 | Lewis et al. |
| 8,177,851 B2 | 5/2012 | Drescher |
| 8,308,810 B2 | 11/2012 | Meridew |
| 8,382,850 B2 | 2/2013 | Della Pria et al. |
| 8,398,718 B2 | 3/2013 | Richardson |
| 8,461,225 B2 | 6/2013 | Muratoglu et al. |
| 8,465,549 B2 | 6/2013 | Richardson |
| 8,530,057 B2 | 9/2013 | Muratoglu et al. |
| 8,679,187 B2 | 3/2014 | Allen et al. |
| 8,790,412 B2 | 7/2014 | McLean et al. |
| 8,801,798 B1 | 8/2014 | Smith |
| 8,843,229 B2 | 9/2014 | Vanasse et al. |
| 8,858,645 B2 | 10/2014 | Grostefon et al. |
| 8,882,849 B2 | 11/2014 | Gradel |
| 8,926,621 B2 | 1/2015 | Liang |
| 8,968,415 B2 | 3/2015 | Meridew et al. |
| 9,107,754 B2 | 8/2015 | Kellar et al. |
| 9,155,819 B2 | 10/2015 | Fonte et al. |
| 9,241,799 B2 | 1/2016 | Grostefon et al. |
| 9,345,585 B2 | 5/2016 | Black |
| 9,364,896 B2 | 6/2016 | Christensen et al. |
| 9,370,878 B2 | 6/2016 | Muratoglu et al. |
| D765,845 S | 9/2016 | Prybyla et al. |
| 9,439,780 B2 | 9/2016 | Witt et al. |
| 9,445,903 B2 | 9/2016 | Meridew et al. |
| 9,445,904 B2 | 9/2016 | Meridew |
| 9,463,093 B2 | 10/2016 | Allen et al. |
| 9,463,094 B2 | 10/2016 | Allen et al. |
| 9,468,529 B2 | 10/2016 | Smith |
| 9,561,306 B2 | 2/2017 | Muratoglu et al. |
| 9,610,164 B2 | 4/2017 | Smith |
| 9,681,955 B2 | 6/2017 | Jordan et al. |
| 9,700,416 B2 | 7/2017 | Grostefon et al. |
| 9,744,047 B2 | 8/2017 | Meridew et al. |
| 9,763,806 B2 * | 9/2017 | Davenport ............ A61F 2/4609 |
| 9,808,347 B2 | 11/2017 | Bailey et al. |
| 9,907,661 B2 | 3/2018 | Ries |
| 9,962,463 B2 | 5/2018 | Muratoglu et al. |
| 9,993,341 B2 | 6/2018 | Vanasse et al. |
| 10,092,406 B2 | 10/2018 | Pressacco |
| 10,307,255 B1 | 6/2019 | Hutton et al. |
| 10,307,267 B2 | 6/2019 | Pritchett |
| 10,314,711 B2 | 6/2019 | Grostefon et al. |
| 10,383,745 B2 | 8/2019 | Allen et al. |
| 10,470,896 B2 | 11/2019 | Huang |
| 2010/0262255 A1 | 10/2010 | Gladdish, Jr. et al. |
| 2012/0101590 A1 | 4/2012 | Preuss et al. |
| 2013/0245782 A1 | 9/2013 | Anapliotis |
| 2014/0324184 A1 | 10/2014 | Bigsby et al. |
| 2014/0371868 A1 | 12/2014 | Anapliotis |
| 2015/0025647 A1 | 1/2015 | Zhang |
| 2016/0015520 A1 | 1/2016 | Smith et al. |
| 2016/0106542 A1 | 4/2016 | Dalla Pria et al. |
| 2018/0214274 A1 | 8/2018 | Perez |
| 2018/0228616 A1 | 8/2018 | Piecuch |
| 2018/0256341 A1 | 9/2018 | Vanasse et al. |
| 2018/0353305 A1 | 12/2018 | Bushell et al. |
| 2019/0053915 A1 | 2/2019 | Macke et al. |
| 2019/0167444 A1 | 6/2019 | Behzadi |
| 2019/0184058 A1 | 6/2019 | Aihara et al. |
| 2019/0254827 A1 | 8/2019 | Rister et al. |
| 2019/0321196 A1 | 10/2019 | Allen et al. |
| 2020/0261232 A1 | 8/2020 | Mistry |

* cited by examiner

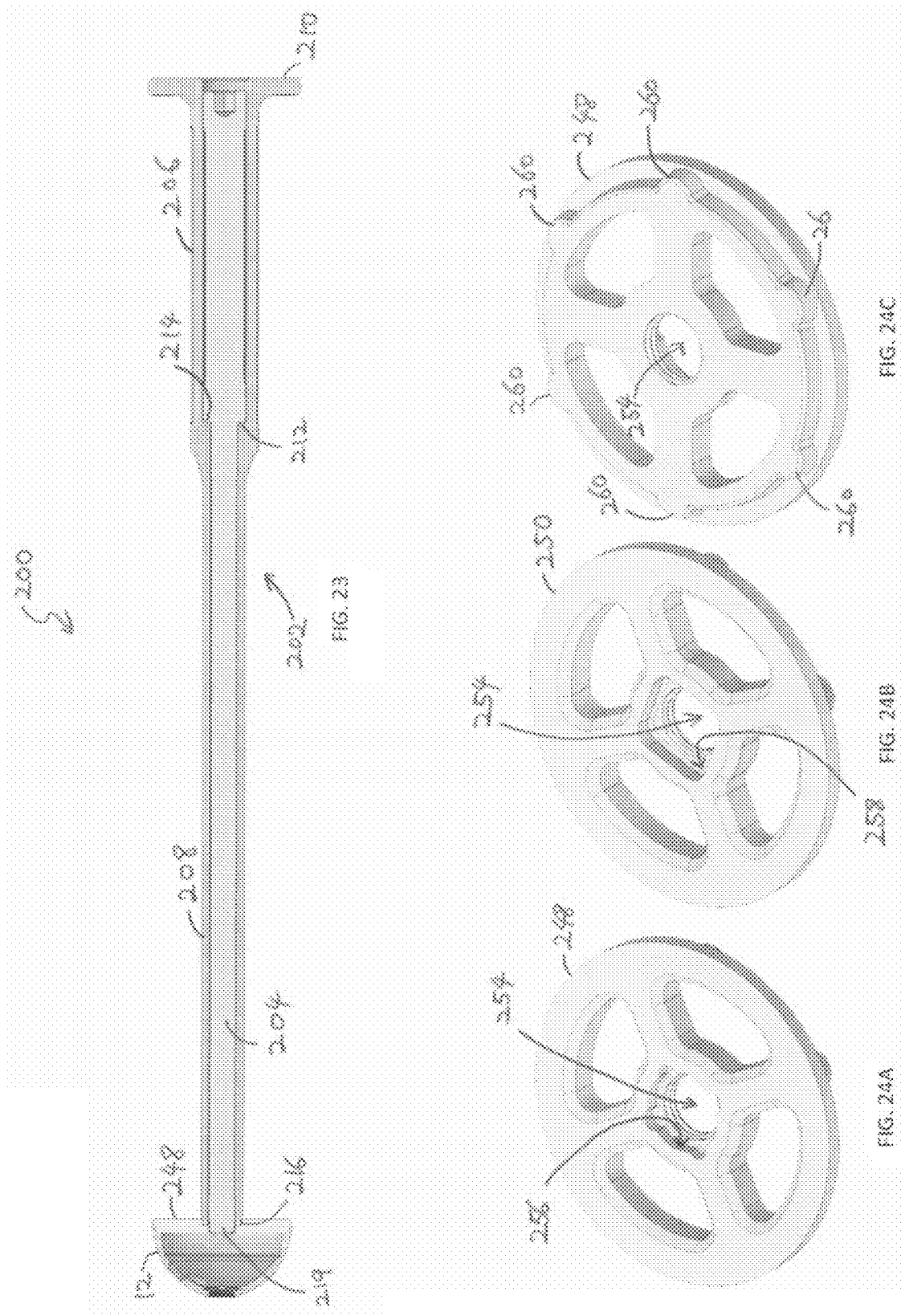

HIP ARTHROPLASTY IMPLANTS

CROSS-REFERENCE TO RELATED APPLICATIONS

The present application is a continuation-in-part of U.S. patent application Ser. No. 17/024,876, filed Sep. 18, 2020, which is incorporated herein by reference.

FIELD

The present disclosure generally relates to hip arthroplasty and, in particular, to hip arthroplasty implants.

BACKGROUND

Hip arthroplasty, often called hip replacement, is a surgical procedure used to reconstruct and resurface a hip joint that has been damaged by disease or injury, such as by arthritis or hip fracture. Total hip arthroplasty devices replace both acetabulum and the femoral head which comprise the hip joint, where the femur articulates relative to the acetabulum. To replace the hip joint, hip arthroplasty includes a femoral implant secured to the end of the femur and an acetabular implant secured to the acetabulum that forms a replacement articulating surface which interfaces with the femoral implant. The femoral implant is pivotably coupled to the acetabular implant, thereby reconstructing the hip joint.

SUMMARY

In one aspect of the present disclosure, an acetabular shell insertion tool with an anti-rotation feature is provided. The insertion tool attaches to an acetabular shell including a center hole having an internal threading and an anti-rotation recess disposed around the center hole and having a predetermined shape. The insertion tool includes an outer shaft and an inner shaft disposed within the outer shaft. The outer shaft has an anti-rotation projection shaped to be received in the anti-rotation recess of the acetabular shell so as to prevent rotation of the outer shaft relative to the acetabular shell, thereby preventing the insertion tool from disengaging from the shell. The inner shaft has a threaded tip adapted to be threaded into the internal threading of the center hole to lock the insertion tool to the acetabular shell.

Other objects and features of the present disclosure will be in part apparent and in part pointed out hereinafter.

BRIEF DESCRIPTION OF THE DRAWINGS

FIG. 23 is a cross-sectional view of a shell insertion tool that attaches to a rim plate according to one aspect the present disclosure;
FIG. 24A to 24C are perspective views of rim plates to which a shell insertion tool attaches according to another aspect the present disclosure.

Figure 1:
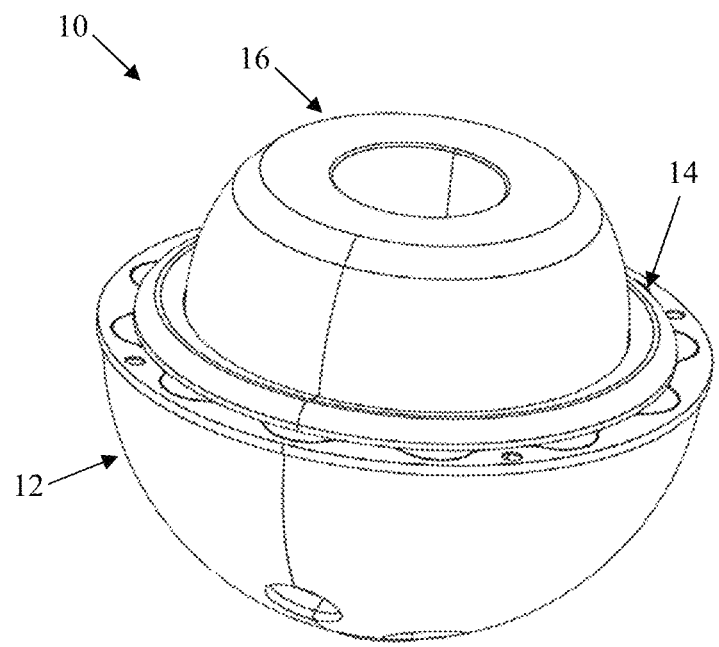
FIG. 1 is a perspective of an acetabular implant according to one embodiment of the present disclosure.

Grayscale shading in the drawings indicates a portion of a component that was cut by a section plane.

Corresponding reference characters indicate corresponding parts throughout the drawings.

DETAILED DESCRIPTION OF THE DISCLOSURE

Various different systems and methods for carrying out and performing hip arthroplasty are disclosed here. The different systems for hip arthroplasty disclosed herein include implants (e.g., acetabular implants and components thereof) and installation or arthroplasty tools for installing the implants. The different methods for hip arthroplasty disclosed herein include methods for installing acetabular implants.

Referring to FIGS. 1-9, an acetabular implant for hip arthroplasty according to one embodiment of the present disclosure is generally indicated at reference numeral 10. In the illustrated embodiment, the implant 10 is a fixed-bearing type implant. The implant 10 includes an acetabular shell 12, an acetabular liner 14 and a femoral head 16. The femoral head 16 is generally spherical, with a spherical outer surface. The femoral head 16 defines a stem cavity 18 sized and shaped to receive a stem (not shown) of a femoral implant (not shown) to couple the femoral head to the femoral implant. In some embodiment, the femoral head 16 may be considered part of the femoral implant.

Figure 4:
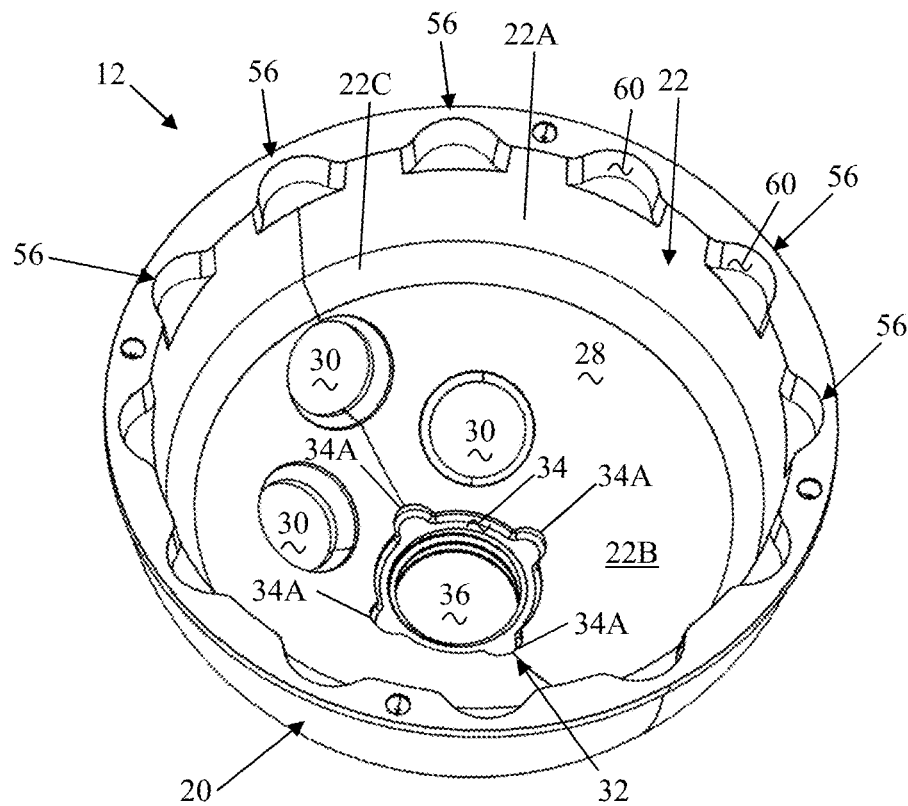
FIG. 4 is a perspective of an acetabular shell of the acetabular implant.
Figure 5:
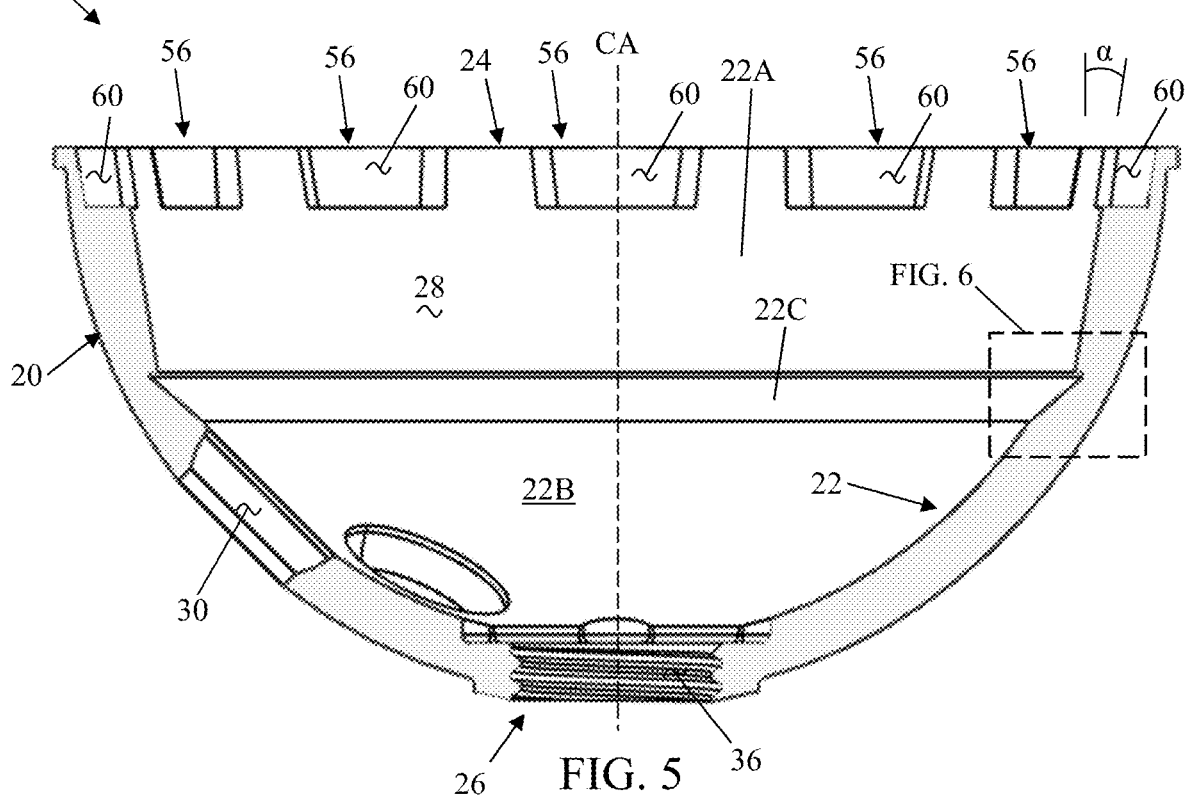
FIG. 5 is a cross section of the acetabular shell.
Figure 6:
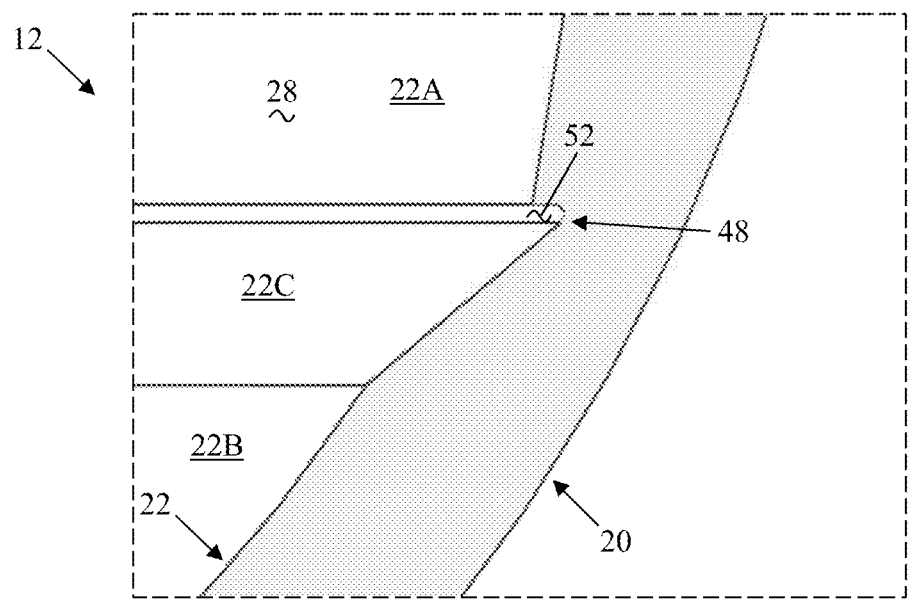
FIG. 6 is an enlarged cross section of the acetabular shell.
Figure 7:
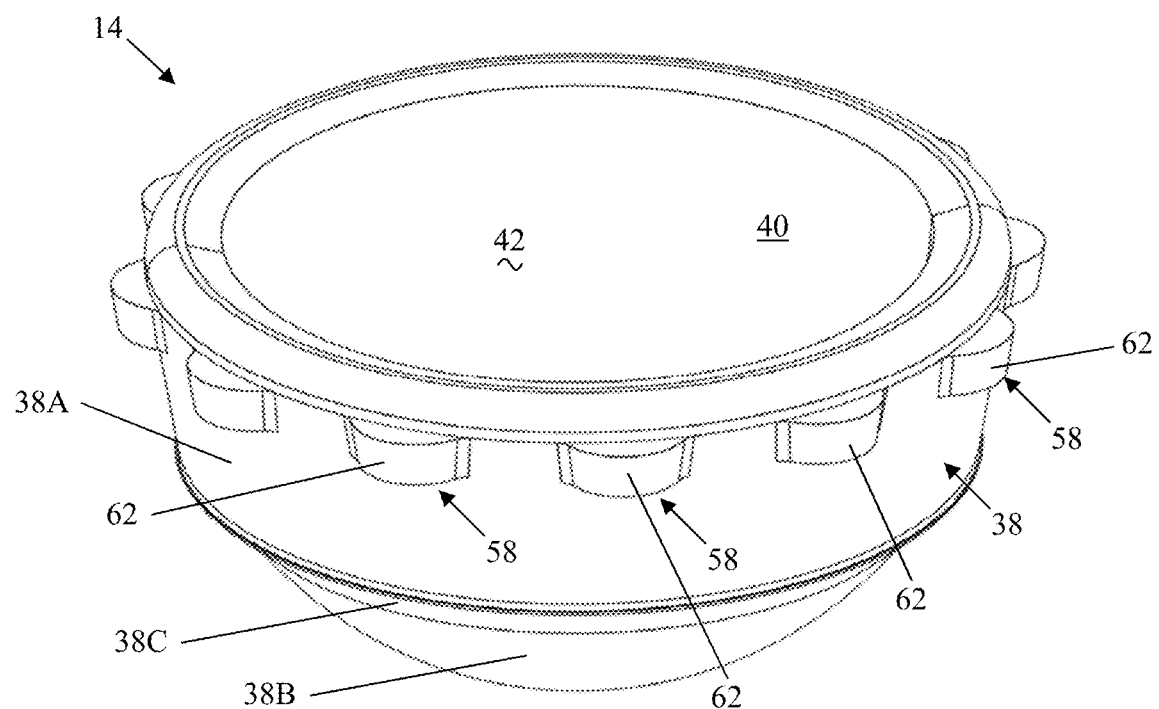
FIG. 7 is a perspective of an acetabular liner of the acetabular implant.
Figure 8:
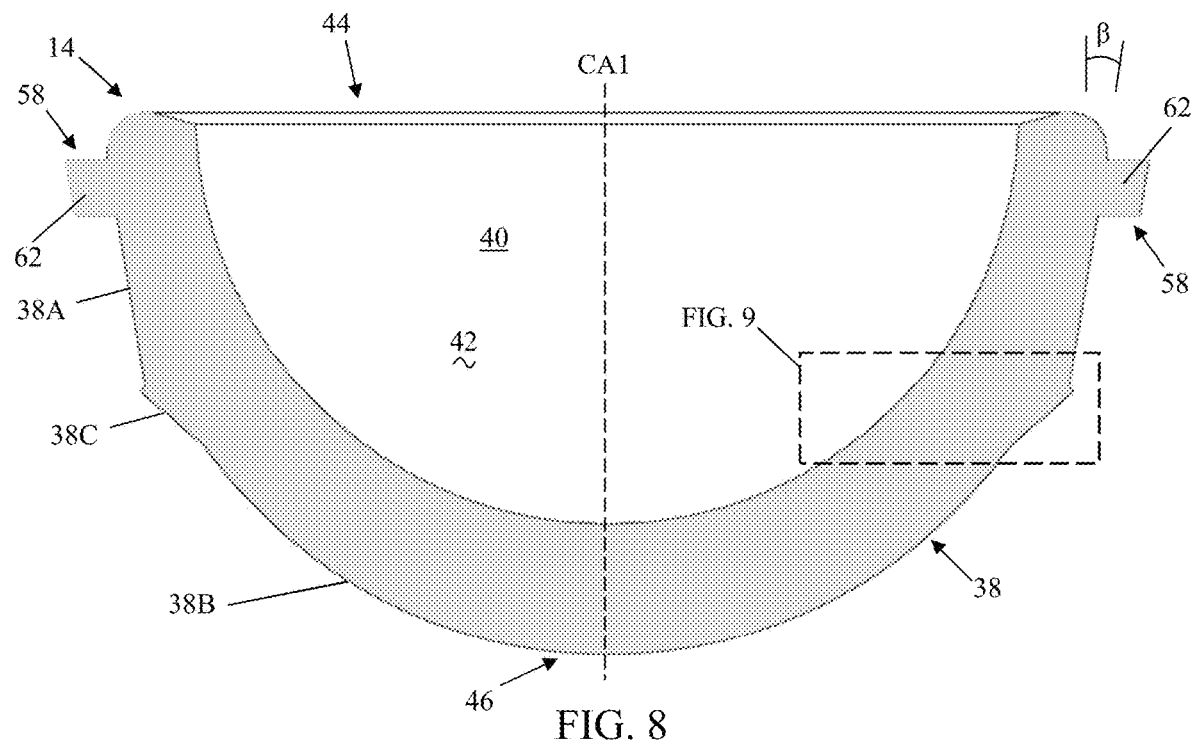
FIG. 8 is a cross section of the acetabular liner.

Referring to FIGS. 4-6, the shell 12 is configured to be attached to an acetabulum (not shown) of a patient. Specifically, the shell 12 is implanted in the acetabulum of the patient. The shell 12 includes a body (e.g., a generally spherical wall) having an outer surface 20 and an inner surface 22. The outer and inner surfaces 20, 22 are generally spherically shaped. The outer surface 20 of the shell 12 is generally semi-spherical. The outer surface 20 may be porous to enable ingrowth of the bone into the shell 12 after the shell is placed in the bone in order to form a strong connection between the shell and the bone. The shell 12 has a proximal end 24 and a distal end 26. The distal end 26 of the shell is generally located at the apex of the spherical body. The shell 12 includes (or defines) a central axis CA (e.g., a shell central axis) extending between the proximal and distal ends 24, 26. The central axis CA generally extends through the apex of the spherical body. The inner surface 22 of the shell 12 defines a shell cavity 28. The shell cavity 28 is sized and shaped to receive the liner 14. The inner surface 22 of the shell 12 includes a tapered shell section 22A, a spherical shell section 22B and a transition shell section 22C generally extending between the tapered shell section and the spherical shell section. The tapered shell section 22A is proximal of the spherical shell section 22B. The tapered shell section 22A tapers inward toward the central axis CA of the shell 12 as the tapered shell section extends distally toward the distal end 26. Thus, the tapered shell section 22A has a generally truncated cone shape. In the illustrated embodiment, the tapered shell section 22A extends distally from the proximal end 24. The tapered shell section 22A tapers at an angle $\alpha$ (as shown in FIG. 5) relative to the central axis CA (e.g., a line parallel to the central axis). Preferably, the angle $\alpha$ of the tapered shell section is within the inclusive range of about 10 degrees to about 30 degrees, and more preferably within the inclusive range of about 15 degrees to about 25 degrees, and more preferably about 19 degrees. For example, in one embodiment, the angle $\alpha$ of the tapered shell section 22A is about 18.8 degrees. The tapered shell section 22A and transition shell section 22C extend circumferentially around the central axis CA. The spherical shell section 22B is generally spherically shaped (e.g., is a partial sphere) with an apex generally aligned with the central axis CA. Other configurations of the shell 12 are within the scope of the present disclosure.

Figure 10:
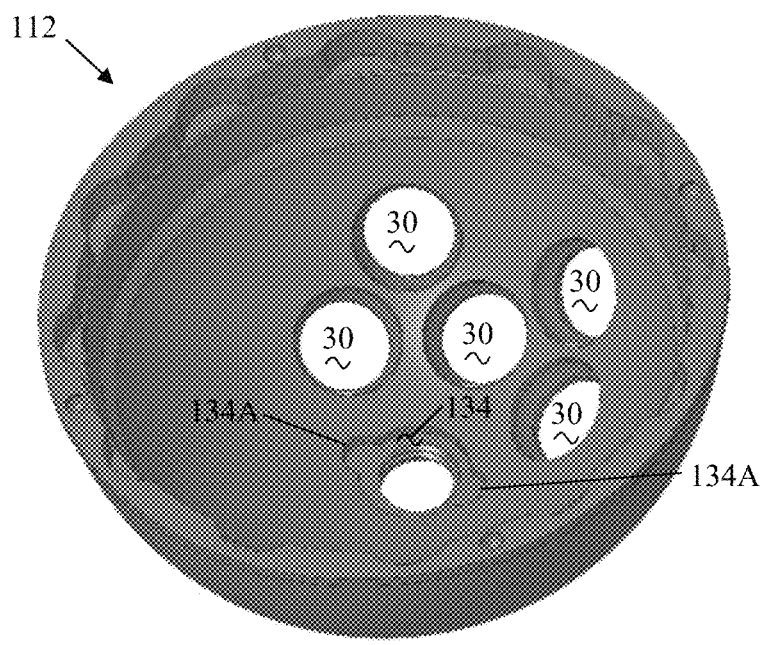
FIG. 10 is a perspective of an acetabular shell according to another embodiment of the present disclosure.
Figure 11:
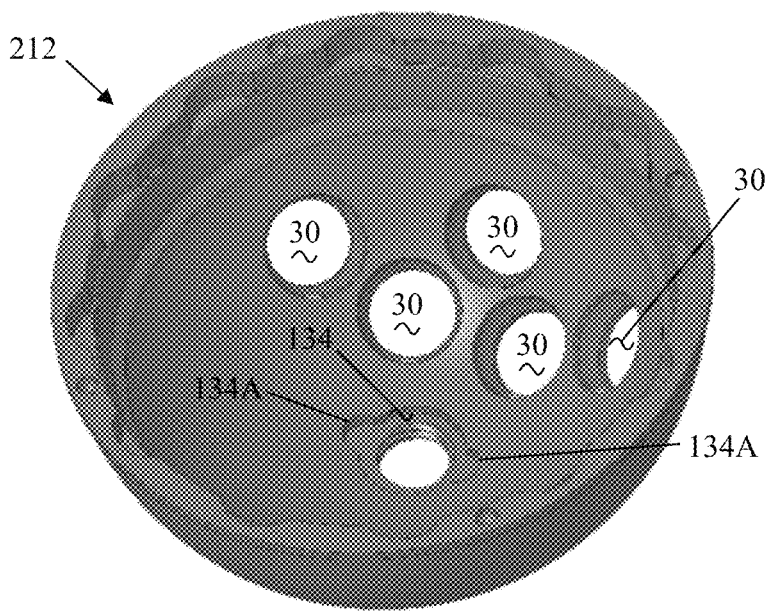
FIG. 11 is a perspective of an acetabular shell according to another embodiment of the present disclosure.

The shell 12 includes (or defines) at least one fastener opening 30. Each fastener opening 30 is sized and shaped to receive a fastener (not shown), such as a bone screw, to secure the shell 12 to the acetabulum. Each fastener opening 30 is disposed in the spherical shell section 22B of the inner surface 22. In the illustrated embodiment, the shell 12 includes three fastener openings 30. The three fastener openings 30 are in a triangle arrangement, although other arrangements are within the scope of the present disclosure. More or fewer fastener openings 30 are also within the scope of the present disclosure. For example, the shell can include five fastener openings 30. One embodiment of a shell 112 having five fastener openings 30 is shown in FIG. 10 and another embodiment of a shell 212 having five fastener openings is shown in FIG. 11. The five fastener openings 30 of shell 112 are arranged in generally an X-shape. The five fastener openings 30 of shell 212 are arranged in generally two circumferential rows stacked on top of each other, with a first row closest to the apex of the spherical shell section 22B having two fastener openings and a second row furthest from the apex having three fastener opening, radially offset from the two fastener openings in the first row. Other numbers and/or arrangements of the fastener openings are within the scope of the present disclosure. The numerous fastener openings 30 give the surgeon flexibility for the placement of the fastener in the acetabulum.

Figure 15:
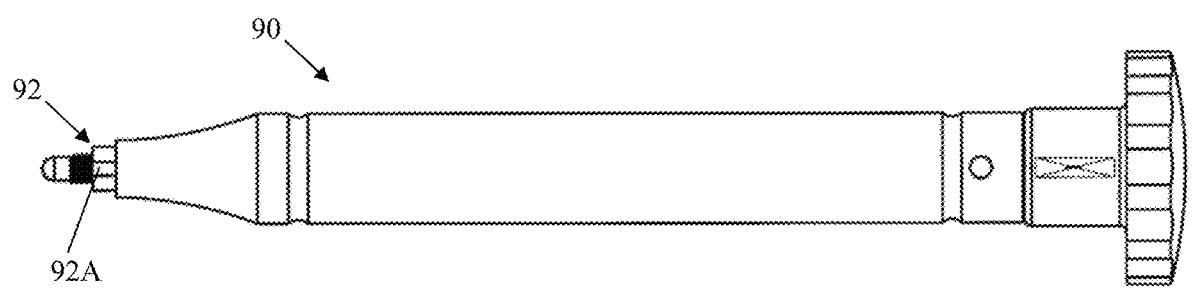
FIG. 15 is a side elevation of shell insertion tool according to one embodiment of the present disclosure.

Referring back to FIG. 4, the shell 12 includes a tool interlocking structure 32. The tool interlocking structure 32 is configured to mate with a shell insertion tool 90 (FIG. 15) to inhibit the shell 12 from rotating relative to the shell insertion tool when the shell and shell insertion tool are coupled together. The shell insertion tool 90 includes threads that mate with threads of the shell 12 (at the apex) to couple the shell and shell insertion tool 90 together. The shell 12 includes a threaded opening 36 disposed at the apex of the spherical shell section 22B, and, thus, is generally aligned with the central axis CA. The shell insertion tool 90 threads into the threaded opening 36 to couple to the shell 12. In the illustrated embodiment, the tool interlocking structure 32 includes an insertion tool recess 34. The insertion tool recess 34 is generally disposed at the apex of the spherical shell section 22B, and, thus, is generally aligned with the central axis CA. The insertion tool recess 34 is sized and shaped to revive a shell projection 92 of the shell insertion tool 90. The insertion tool recess 34 includes at least one rotation inhibiting section 34A (e.g., lobe). In the illustrated embodiment, the insertion tool recess 34 includes four rotation inhibiting sections 34A, although more or fewer are within the scope of the present disclosure. Each rotation inhibiting section 34A is sized and shaped to receive a rotation inhibiting structure 92A (e.g., projection) of the shell insertion tool to inhibit the shell 12 from rotating about the central axis CA when the shell and shell insertion tool 90 are coupled together. Each rotation inhibiting section 34A is offset from the central axis CA. When the shell insertion tool 90 and the shell 12 are coupled together, the shell projection 92 extends into (e.g., mates or registers with) the insertion tool recess 34 (e.g., each rotation inhibiting structure 92A extends into one of the rotation inhibiting sections 34A). The engagement between the shell projection 92 and the shell 12 at the insertion tool recess 34 (e.g., the rotation inhibiting structure 92A and the shell at the rotation inhibiting section 34A), prevents the shell from inadvertently rotating (e.g., about the central axis CA) and potentially uncoupling (e.g., unthreading) from the shell insertion tool 90, especially if the inserter tool has not been threaded into the central threaded hole of the shell 12.

The insertion tool recess 34 may have generally any shape. In the illustrated embodiment, the insertion tool recess 34 has a generally circular shape with four rotation inhibiting sections 34A extending radially outward from a circumference of the circle at equally spaced intervals. Other configurations of the tool interlocking structure 32 are within the scope of the present disclosure. For example, the insertion tool recess can have other shapes and sizes. It is understood whatever the shape and size of the insertion tool recess, the shell projection of the shell insertion tool 90 has a corresponding (e.g., confirming, matching) size and shape.

In one example, referring to FIGS. 10 and 11, an insertion tool recess for a shell 112, 212 according to another embodiment of the present disclosure is generally indicated at reference numeral 134. In this embodiment, the insertion tool recess 134 has a generally circular shape with two rotation inhibiting sections 134A extending radially outward from a circumference of the circle on generally opposite sides thereof.

Figure 12:
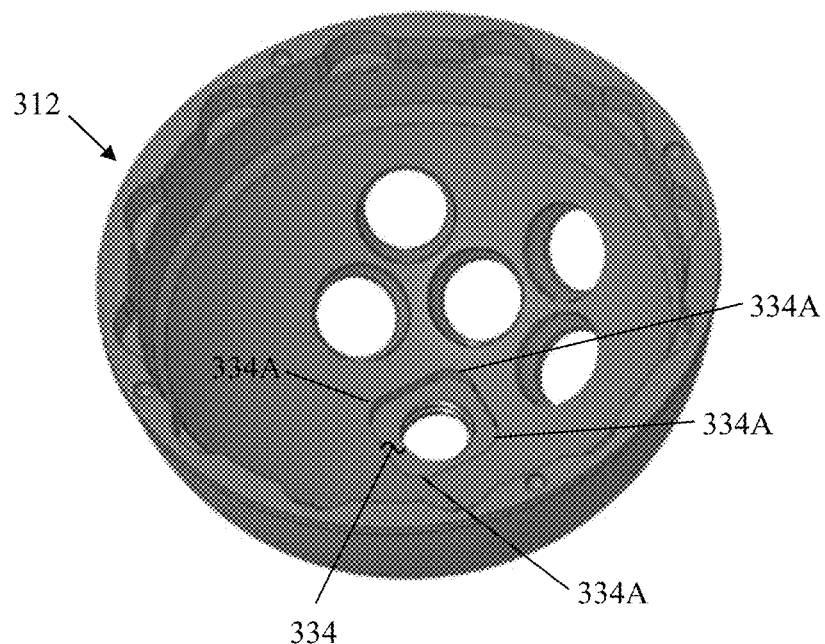
FIG. 12 is a perspective of an acetabular shell according to another embodiment of the present disclosure.

Referring to FIG. 12, an insertion tool recess for a shell 312 according to another embodiment of the present disclosure is generally indicated at reference numeral 334. In this embodiment, the insertion tool recess 334 has a generally polygonal (e.g., rectangular, square, etc.) shape with the corners (e.g., rounded corners) forming the rotation inhibiting sections 334A. Other polygonal shapes are within the scope of the present disclosure.

Figure 13:
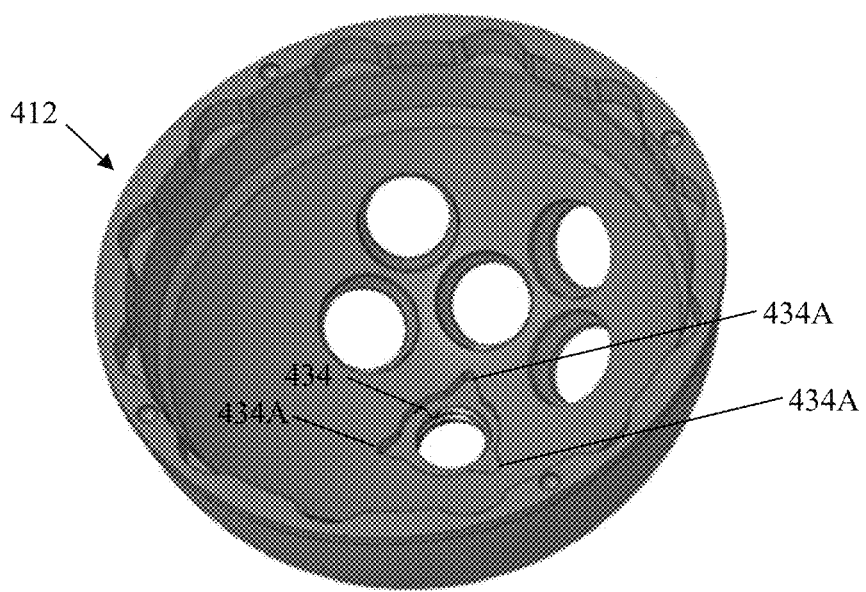
FIG. 13 is a perspective of an acetabular shell according to another embodiment of the present disclosure.

Referring to FIG. 13, an insertion tool recess for a shell 412 according to another embodiment of the present disclosure is generally indicated at reference numeral 434. In this embodiment, the insertion tool recess 434 has a generally triangular shape, with a generally center circle shaped section and three rotation inhibiting sections 434A, having generally triangular or trapezoidal shapes extending radially outward from the circle shaped section at equally spaced intervals.

Figure 14:
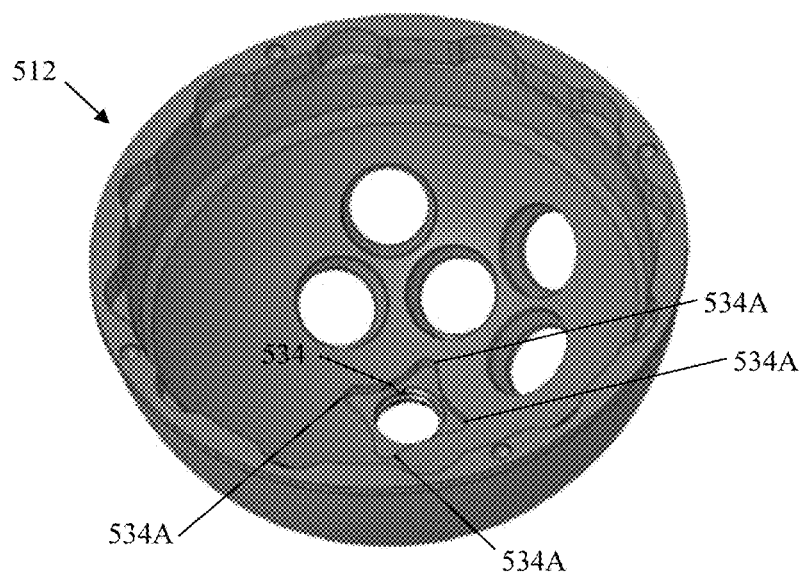
FIG. 14 is a perspective of an acetabular shell according to another embodiment of the present disclosure.

Referring to FIG. 14, an insertion tool recess for a shell 512 according to another embodiment of the present disclosure is generally indicated at reference numeral 534. In this embodiment, the insertion tool recess 534 has a generally star shape (e.g., rounded star shape) with the points of the star shape forming the rotation inhibiting sections 534A. In the illustrated embodiment, the star shape of the insertion tool recess 534 has four points, although more or fewer points are within the scope of the present disclosure.

Referring back to FIGS. 7-9, the liner 14 of the implant 10 is configured to be attached to the shell 12. In particular, the liner 14 is sized and shaped to be disposed in the shell cavity 28 of the shell 12 (e.g., the shell cavity is sized and shaped to receive the liner). The liner 14 includes a body (e.g., a generally spherical wall) having an outer surface 38 and an inner surface 40. The outer and inner surfaces 38, 40 are generally spherically shaped. The inner surface 40 defines a liner cavity 42. The liner cavity 42 is sized and shaped to receive at least one of a mobile insert, as described in more detail below, or the femoral head 16. In the illustrated embodiment, the liner cavity 42 is sized and shaped to receive the femoral head 16. The inner surface 40 is generally semi-spherical. The inner surface 40 is smooth to permit the mobile insert or femoral head 16 received in the liner cavity 42 to articulate or pivot relative to the liner 14. Optionally, the inner surface 40 may be polished to a mirror finish, especially if the part is metal. The liner 14 has a proximal end 44 and a distal end 46. The distal end 46 of the liner 14 is generally located at the apex of the spherical body. The liner 14 includes (e.g., defines) a central axis CA1 (e.g., a liner central axis) extending between the proximal and distal ends 44, 46. The central axis CA1 generally extends through the apex of the spherical body. When the liner 14 is coupled to the shell 12 (e.g., disposed in the shell cavity 28) the central axes CA, CA1 of the liner and shell are generally coextensive with one another.

The outer surface 38 of the liner 14 includes a tapered liner section 38A, a spherical liner section 38B and a transition liner section 38C generally extending between the tapered liner section and the spherical liner section. The tapered liner section 38A is proximal of the spherical liner section 38B. The spherical liner section 38B generally corresponds (e.g., is generally sized and shaped to conform) to the spherical shell section 22B of the shell 12. Because a snap-fit receiver 48 (see FIG. 6) and a snap-fit retainer 50 (see FIG. 9) form a snap-fit connection between the shell and the liner when the liner is inserted into the shell cavity 28 of the shell, the liner 14 has been designed to have a small clearance between the spherical liner section 38B and the spherical shell section 22B. Specifically, the clearance is at least 0.1 mm and at most 0.4 mm in one embodiment. The clearance provides the benefit of less rubbing between the liner 14 and the shell 12 to reduce the possibility of any shaving which could be detrimental to the patient.

The spherical shell section 38B is generally spherically shaped (e.g., is a partial sphere) with an apex generally aligned with the central axis CA. The transition liner section 38C generally corresponds (e.g., is generally sized and shaped to conform) to the transition shell section 22C of the shell 12 such that the transition liner section and the transition shell section generally mate (e.g., engage) when the liner 14 is coupled to the shell. In addition, the tapered liner section 38A generally corresponds (e.g., is generally sized and shaped to conform) to the tapered shell section 22A of the shell 12 such that the tapered liner section and the tapered shell section generally mate (e.g., engage) when the liner 14 is coupled to the shell. The tapered liner section 38A has a taper that corresponds to (e.g., matches) the taper of the tapered shell section 22A of the shell 12. The tapered liner section 38A tapers inward toward the central axis CA1 of the liner 14 as the tapered liner section extends distally toward the distal end 46. Thus, the tapered liner section 38A has a generally truncated cone shape. In the illustrated embodiment, the tapered liner section 38A extends distally from the proximal end 44. The tapered liner section 38A tapers at an angle β (FIG. 8) relative to the central axis CA1 (e.g., a line parallel to the central axis). Preferably, the angle β of the tapered shell section is within the inclusive range of about 10 degrees to about 30 degrees, and more preferably within the inclusive range of about 15 degrees to about 25 degrees, and more preferably about 19 degrees. Preferably, the angle β is slightly greater than the angle α of the taper of the tapered shell section 22A. For example, in one embodiment, the angle β of the tapered liner section 38A is about 19 degrees. The slightly larger angle β than the angle α ensures the tapered liner section 38A is received by and engages the tapered shell section 22A in an interference fit. The tapered liner section 38A is configured to engage the tapered shell section 22A to inhibit movement of the liner 14 relative to the shell 12 when the liner is disposed in the shell cavity 28 of the shell. When coupled together, the tapered liner section 38A and the tapered shell section 22A engage each other to inhibit the liner 14 from moving relative to the shell 12. Specifically, the engagement of the tapered liner section 38A and the tapered shell section 22A inhibits the liner 14 from rotating, about an axis of rotation perpendicular to the central axes CA, CA1, relative to the shell 12. The tapered liner section 38A and transition liner section 38C extend circumferentially around the central axis CA1. Other configurations of the liner are within the scope of the present disclosure.

The liner 14 constructed using (e.g., may be made from) any suitable material, such as a plastic, a metal (such as a cobalt-chrome alloy), or a ceramic. In certain applications, such as a dual mobility application (discussed in more detail below), constructing the liner from a ceramic may be preferred because ceramic is harder and smoother than metal, providing a better wear or bearing surface (e.g., inner surface 38 and or inner surface 40). Ceramic liners are also better at preventing particles from being generated due to micro-motion between the liner 14 and the shell 12, then metal liners.

Figure 2:
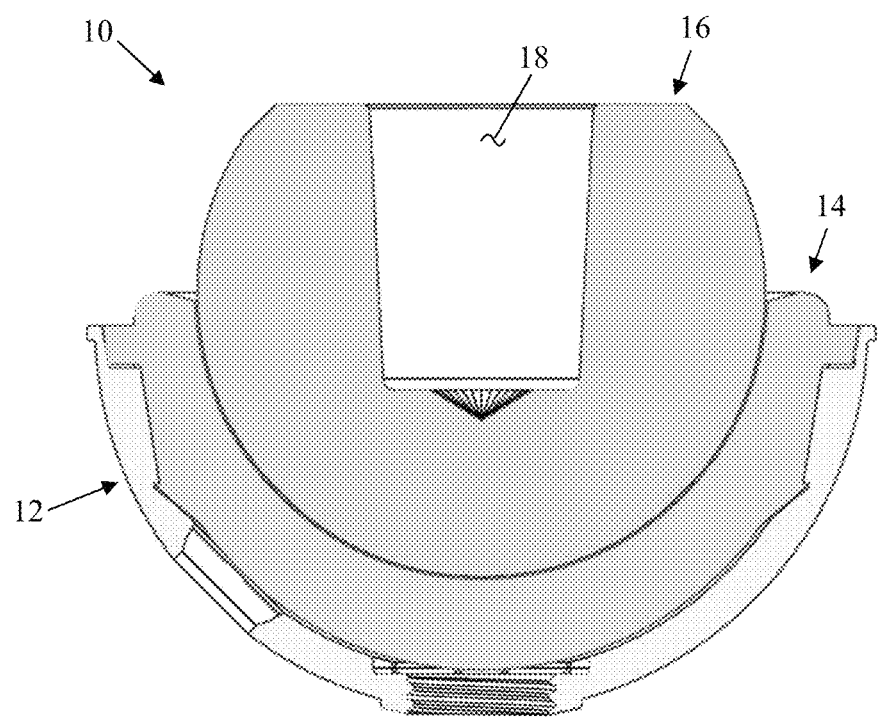
FIG. 2 is a cross section of the acetabular implant.
Figure 3:
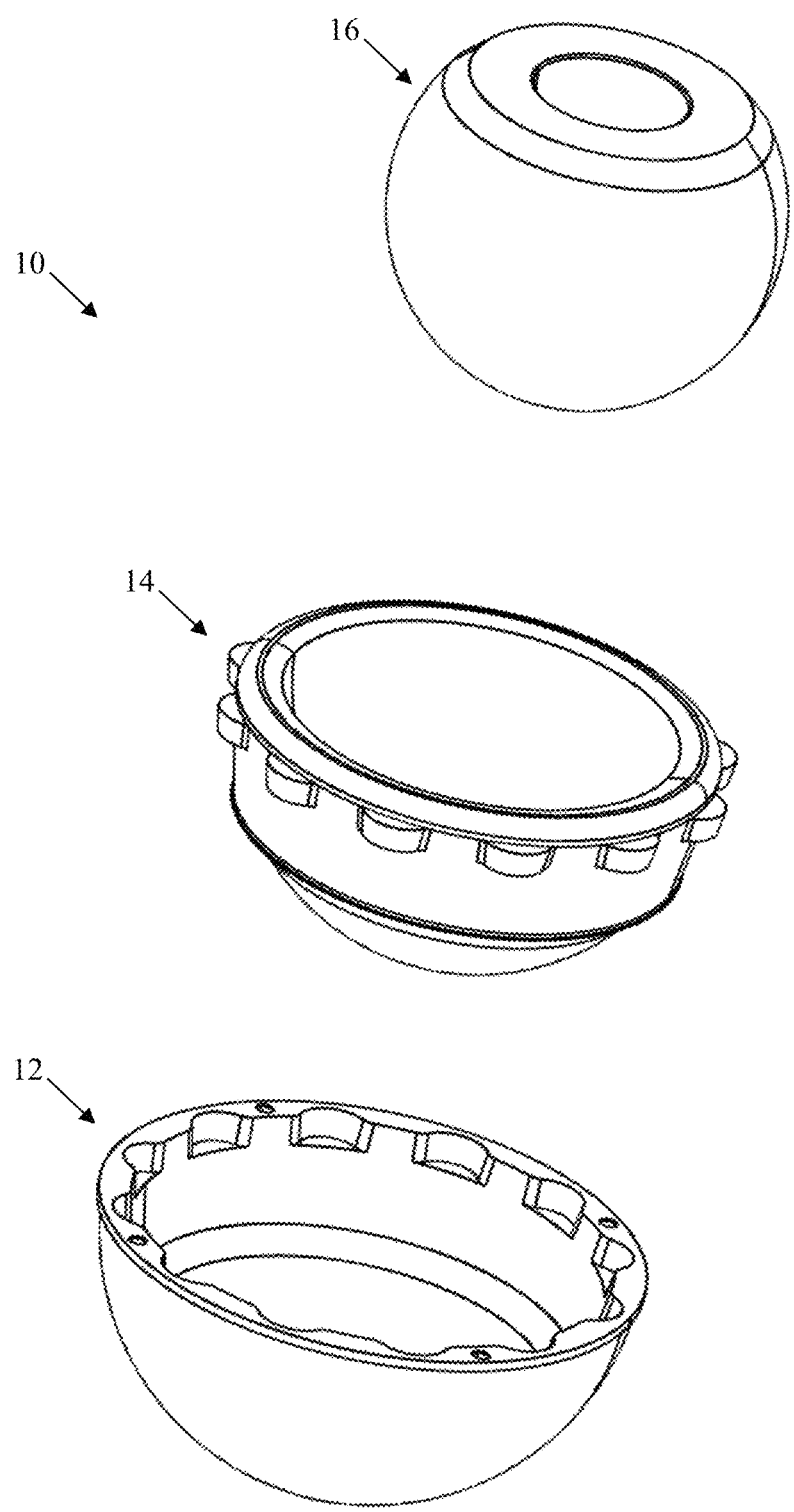
FIG. 3 is an exploded view of the acetabular implant.
Figure 9:
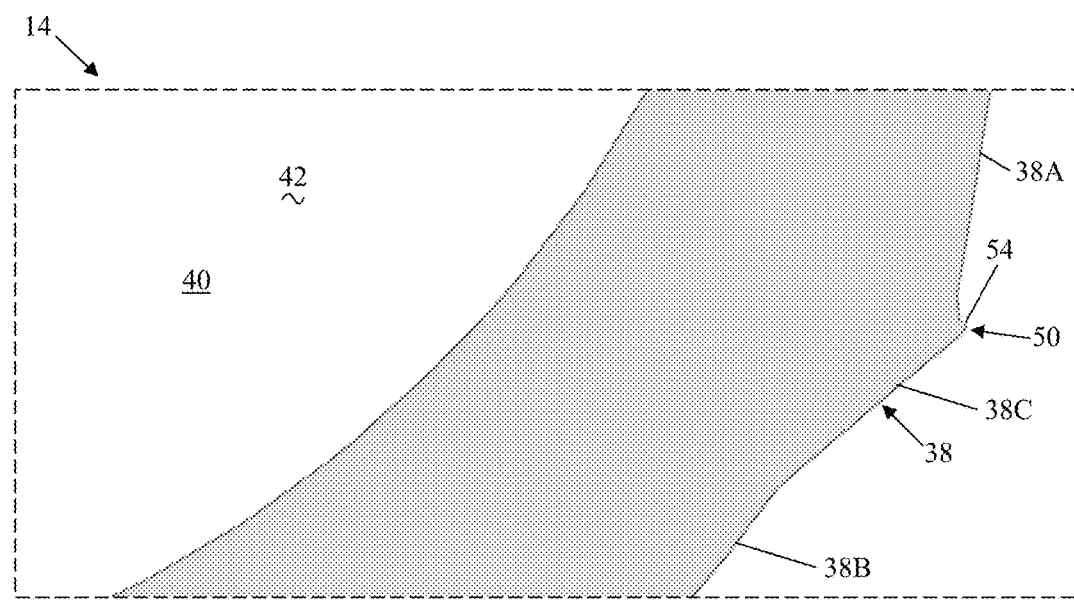
FIG. 9 is an enlarged cross section of the acetabular liner.

Referring to FIGS. 2, 6 and 9, the shell 12 and the liner 14 have corresponding connectors that secure the shell and liner together when the liner is disposed in the shell cavity 28 of the shell. In the illustrated embodiment, the shell 12 and liner 14 form a snap-fit connection therebetween to couple and secure the shell and liner together. The shell 12 includes a snap-fit receiver 48 and the liner 14 includes a snap-fit retainer 50 sized and shaped to be received by the snap-fit receiver to form the snap-fit connection between the shell and the liner when the liner is inserted into the shell cavity 28 of the shell. The snap-fit receiver 48 includes a generally circumferential recess 52 and the snap-fit retainer 50 includes a generally circumferential lip 54 (e.g., detent, catch) that is sized and shaped to be received by (e.g., inserted into) the recess. The circumferential recess 52 and the circumferential lip 54 extend circumferentially around the central axes CA, CA1. The lip 54 is resiliently deflectable to permit the liner 14 to be inserted into the shell cavity 28 of the shell 12. As the liner 14 is inserted distally into the shell cavity 28 of the shell 12, the shell (e.g., tapered shell section 22A) deflects or deforms the lip 54. Once the lip 54 is aligned with the recess 52, the lip returns or snaps-back to its undeformed state (FIG. 9), extending into the recess and forming the snap-fit connection securing the liner to the shell (FIG. 2). Other configurations of the connectors securing the shell and liner together are within the scope of the present disclosure.

Referring to FIGS. 2, 4, 5, 7 and 9, the shell 12 and the liner 14 may include corresponding interlocking structures to inhibit movement (e.g., rotation) of the shell and liner relative to one another. In the illustrated embodiment, the shell 12 includes at least one shell interlocking structure 56 and the liner 14 includes at least one liner interlocking structure 58. Preferably, the shell 12 includes a plurality of shell interlocking structures 56 and the liner 14 includes a plurality of liner interlocking structures 58. In the illustrated embodiment, the shell 12 includes twelve shell interlocking structures 56 and the liner 14 includes twelve liner interlocking structures 58, although more or fewer shell and liner interlocking structures are within the scope of the present disclosure. For example, the shell can include six shell interlocking structures and the liner can include six liner interlocking structures. The plurality of shell interlocking structures 56 are circumferentially spaced apart from one another (about the central axis CA of the shell 12). Likewise, the plurality of liner interlocking structures 58 are circumferentially spaced apart from one another (about the central axis CA1 of the liner 14). Each shell interlocking structure 56 is configured to mate (e.g., interlock) with one of the liner interlocking structures 58 to inhibit rotation of the liner 14 relative to the shell 12 about the central axes CA, CA1 when the liner is disposed in the shell cavity 28 of the shell. The shell interlocking structure 56 includes an interlocking recess 60 and the liner interlocking structure 58 includes an interlocking projection 62 that is sized and shaped to be received by the interlocking recess. In other words, the interlocking recess 60 and interlocking projection 62 have corresponding (e.g., matching) shapes and sizes. In the illustrated embodiment, the shell interlocking structures 56 are disposed generally adjacent the proximal end 24 of the shell 12. The liner interlocking structures 58 are also disposed generally adjacent the proximal end 44 of the liner 14. When the shell 12 and liner 14 are coupled together, each interlocking projection 62 extends into (e.g., mates, registers or interlocks with) one of the interlocking recesses 60. The engagement between the interlocking projections 62 of the liner 14 and the shell 12 at the interlocking recesses 60, prevents the liner from inadvertently rotating (e.g., about the central axes CA, CA1) relative to the shell.

Figure 16:
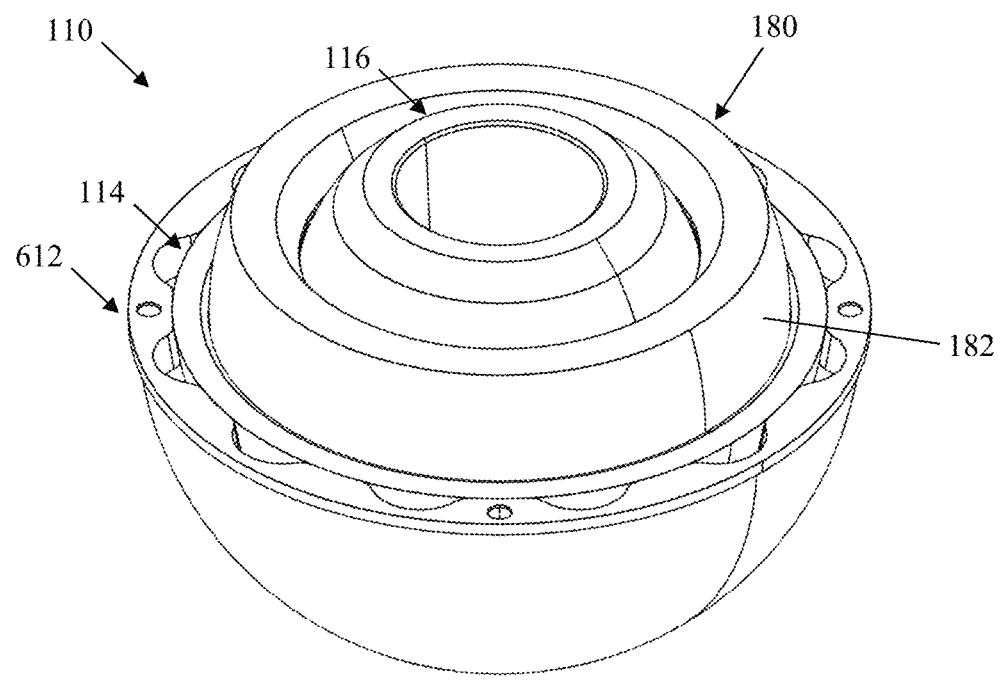
FIG. 16 is a perspective of an acetabular implant according to another embodiment of the present disclosure.
Figure 17:
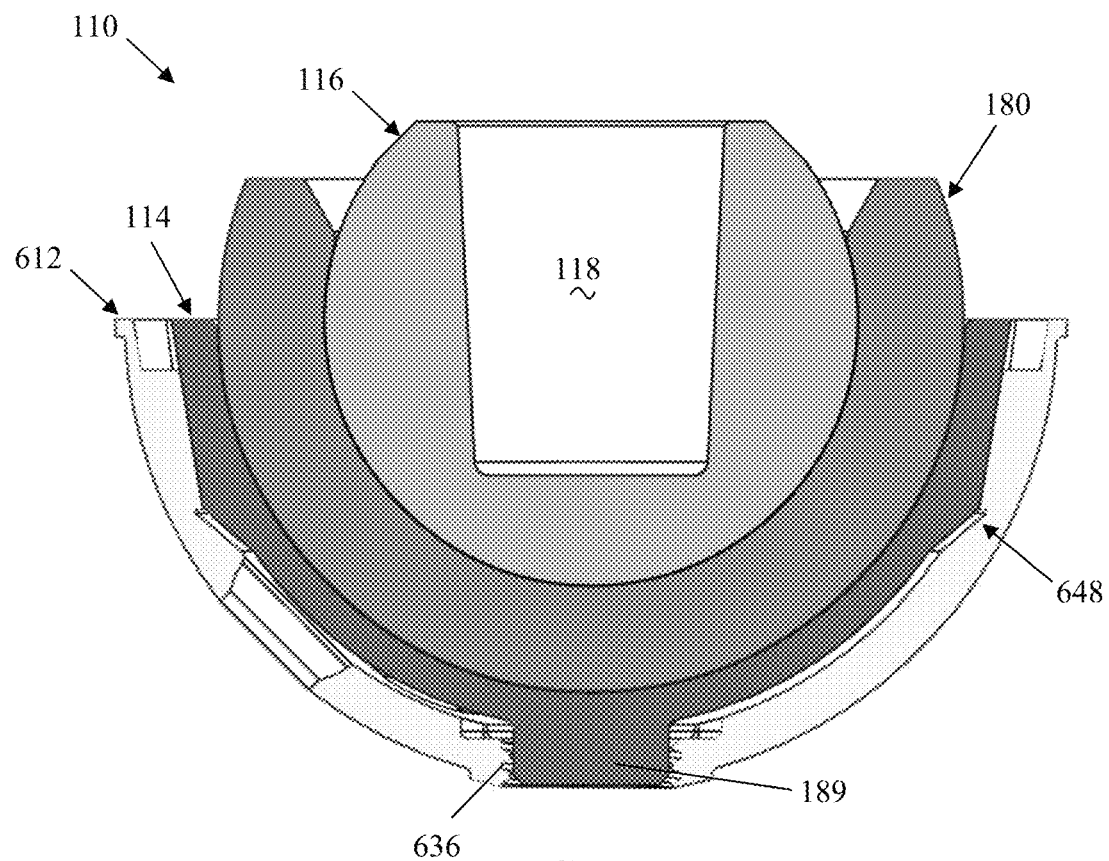
FIG. 17 is a cross section of the acetabular implant of FIG. 16.
Figure 18:
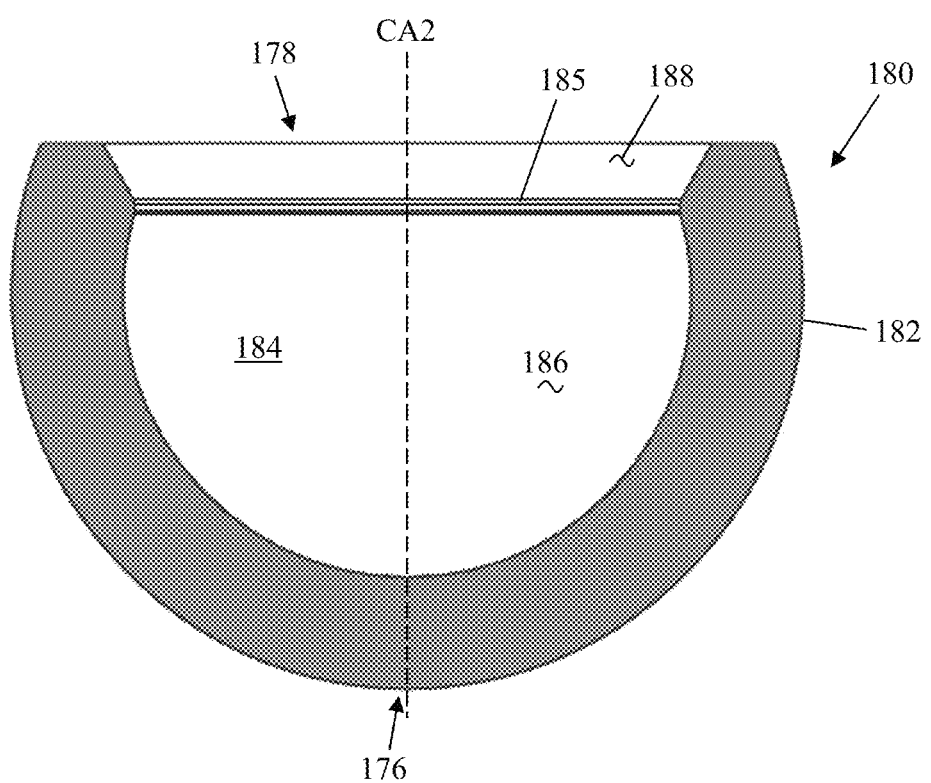
FIG. 18 is a cross section of a mobile insert of the acetabular implant of FIG. 16.

Referring to FIGS. 16-18, another embodiment of an acetabular implant according to the present disclosure is generally indicated by reference numeral 110. Implant 110 is generally analogous to implant 10 and, thus, unless clearly stated or indicated otherwise, the descriptions herein regarding implant 10 (and elements thereof such as shell 12 and liner 14) also apply to implant 110. In this embodiment, the main difference between implant 10 and implant 110 is that implant 110 is a dual mobility type implant. Accordingly, the implant 110 further includes a mobile insert 180. The mobile insert 180 is disposed between the liner 114 and the femoral head 116 and can articulate (e.g., rotate) relative to both the liner and the femoral head.

The mobile insert 180 is configured to couple to both the liner 114 and the femoral head 116. In particular, the mobile insert 180 is sized and shaped to be disposed (e.g., received) in the liner cavity 142 of the liner 114. In this embodiment, the liner cavity 142 of the liner 114 is sized and shaped to receive the mobile insert 180. The mobile insert 180 includes a body (e.g., a generally spherical wall) having an outer surface 182 and an inner surface 184. The mobile insert 180 has a proximal end 178 and a distal end 176 (at generally the apex of the spherical body) with a central axis CA2 (e.g., a mobile insert central axis) extending therebetween (and through the apex of the spherical body). In the position shown in FIG. 17, the central axis CA2 (see FIG. 18) of the mobile insert 180 is generally coextensive with the central axes CA, CA1 of the shell 612 and the liner 114. The outer and inner surfaces 182, 184 are generally spherically shaped. The outer surface 182 is smooth to permit the mobile insert 180 to articular or pivot relative to the liner 114 (e.g., slide on the inner surface 140 of the liner). The spherical outer surface 182 forms the majority of a sphere. For example, in one embedment, the height (extending between the proximal and distal ends 178, 176) of the mobile insert 180 (e.g., height of the outer surface 182) is within the inclusive range of about 55% to about 75% of an outer diameter of the mobile insert (e.g., diameter of the outer surface), or more preferably within the inclusive range of about 60% to about 70% of the outer diameter, or even more preferably about 65% of the outer diameter. This larger outer surface 182 increases the range of motion between the mobile insert 180 and the liner 114 over conventional mobile inserts that are typically only semi-spherical.

The inner surface 184 of the mobile insert 180 defines a mobile insert cavity 186 sized and shaped to receive the femoral head 116. The inner surface 184 is smooth to permit the mobile insert 180 to articular or pivot relative to the femoral head 116 (e.g., permit the femoral head to slide on the inner surface of the mobile insert). The mobile insert 180 is configured to attach to the femoral head 116 to prevent the mobile insert and femoral head from decoupling from one another. In the illustrated embodiment, the mobile insert 180 is configured to form a snap-fit connection with the femoral head 116. The inner surface 184 has a proximal rim 185. The inner surface 184 generally extends proximally, in a spherical manner, from an apex of the sphere to the proximal rim 185. In the illustrated embodiment, the proximal rim 185 is distal of the proximal end 178. Like the outer surface 182, the inner surface 184 forms the majority of a sphere. For example, in one embedment, the height (between the apex of the spherical inner surface 184 and the proximal rim 185 and extending parallel to the central axis CA2) of the inner surface 183 (e.g., a height of the mobile insert cavity 186) is within the inclusive range of about 55% to about 75% of an inner diameter of the inner surface 184, or more preferably within the inclusive range of about 60% to about 70% of the inner diameter, or even more preferably about 65% of the inner diameter. As a result, a proximal portion of the inner surface 184 generally tapers toward the central axis CA2 as it extends proximally toward the proximal rim 185. This proximal portion of the inner surface 184 retains the femoral head 116 in the mobile cavity 186. Thus, the inner surface 184 surrounds a majority of the spherical femoral head 116 to retain the femoral head in the mobile insert cavity 186. The mobile insert 180 is constructed using a resiliently deflectable material. Accordingly, the mobile insert 180 (e.g., proximal rim 185) is resiliently deflectable to permit the femoral head 116 to inserted into the mobile insert cavity 186. As the femoral head 116 is inserted distally into the mobile insert cavity 186, the mobile insert deflects or deforms (e.g., the proximal rim 185 expands radially outward) to enlarge the proximal end of the mobile insert cavity to permit the femoral head to pass therethrough. Once the femoral head 116 is in the mobile insert cavity 186 (e.g., the widest part of the femoral head has passed the proximal rim 185), the mobile insert 180 returns or snaps-back to its undeformed state (FIG. 18), forming the snap-fit connection and securing the femoral head to the mobile insert. In one embodiment, an insertion tool or press (not shown) may be required to insert the femoral head 116 into the mobile insert cavity 186.

The mobile insert 180 may also include a stem relief recess 188 at a proximal end of the mobile insert cavity 186. The stem relief recess 188 is configured to receive (intermittently receive as need) a stem (not shown) of the femoral implant when the femoral implant (e.g., femoral head 116) rotates relative to the mobile insert 180. This increases the possible range of motion between the femoral implant and the mobile insert 180. In the illustrated embodiment, the stem relief recess 188 is generally defined by an inner circumferential chamfer (e.g., a tapered inner surface) of the mobile insert 180 extending between the proximal rim 185 and the proximal end 178 of the mobile insert. Other configurations of the mobile insert 180 are within the scope of the present disclosure.

In addition to the mobile insert 180, the implant 110 has a liner 114 with a different configuration. The liner 114 does not includes a snap-fit retainer, such as snap-fit retainer 50, to secure the liner to the shell 612. In this embodiment, the liner 114 is preferably made of a ceramic or metallic alloy such as cobalt chrome alloy, which may be generally unsuitable for forming a snap-fit retainer (e.g., the snap-fit retainer may break instead of resiliently deforming when inserted into the shell 612). In the illustrated embodiment, the shell 612 still includes a snap-fit receiver 648, although in other embodiments, the snap-fit receiver may also be eliminated from the shell. In addition, in this embodiment, the liner 114 does not include liner interlocking structures 58. In the illustrated embodiment, the shell 612 still includes the shell interlocking structures 56, although in other embodiment, the shell interlocking structures may also be eliminated from the shell. Moreover, in this embodiment, the liner 114 includes an alignment projection 189. The alignment projection 189 generally extends distally from the apex of the spherical outer surface 138 of the liner 114. The alignment projection 189 is configured to be inserted into the threaded opening 636 (broadly, an alignment recess) of the shell 612. It is understood the alignment projection 189 could be configured to extend into a different recess (e.g., opening) of the shell 612. The insertion of the alignment projection 189 into the alignment recess 612 facilitates the alignment and positioning (e.g., centering) of the liner 114 relative to the shell 612 when the liner is being coupled to the shell.

In operation, to implant an acetabular implant, such as implant 10, into the acetabulum of a patient, first the surgeon prepares the acetabulum to receive the shell 12 of the implant. Preparing the acetabulum may include one or more of reaming, cutting, and the like to shape the acetabulum to receive the shell 12. After, the surgeon couples the shell 12 to the shell insertion tool 90. This may be done by threading the shell 12 onto the threads of the shell insertion tool. Coupling the shell 12 to the shell insertion tool 90 includes inserting the shell projection 92 of the shell insertion tool into the tool interlocking structure 32 (e.g., insertion tool recess 34) of the shell. The mating of the tool interlocking structure 32 with the shell insertion tool 90 (e.g., shell projection 92) while the shell and shell insertion tool are coupled together inhibits the rotation (and inadvertent decoupling) of the shell relative to the shell insertion tool, in particular while the shell is being implanted. The surgeon then uses the shell insertion tool 90 to implant the shell 12. The surgeon generally moves the shell insertion tool 90, with the shell 12 thereon, distally into the prepared section of the acetabulum. The surgeon may use a hammer (not shown) to contact the shell insertion tool 90 and drive the shell 12 into the acetabulum. After the shell 12 is in position, the surgeon detaches the shell insertion tool 90 from the shell 12, This requires the disengagement (e.g., removal) of the shell projection 92 from the tool interlocking structure 32 and then unthreading (e.g., rotating) the shell insertion tool 90 from the shell 12. If desired, the surgeon can then insert one or more fasteners (not shown) through the one or more fastener openings 30 to secure the shell 12 to the acetabulum.

The liner 14 is then inserted into the shell cavity 28 of the shell 12. The liner 14 is moved distally into the shell cavity 28. If the liner includes an alignment projection 189, such as liner 114, the surgeon aligns the alignment projection with the alignment recess 36, 136 (e.g., the threaded opening in the illustrated embodiment). As the surgeon moves the liner 114 distally, the alignment projection 189 moves distally into the alignment recess 36, 136. Insertion of the liner 14 also includes mating the one or more liner interlocking structures 58 with the one or more shell interlocking structures 56. The surgeon rotates the liner 14 about the central axis CA1, such that the liner interlocking structures 58 align with the shell interlocking structures 56. As the liner 14 is moved distally, the liner interlocking structures 58 mate with the shell interlocking structures 56. Specifically, each liner interlocking projection 62 moves into one of the interlocking recesses 60 (through an open proximal side thereof). The mating of the shell and liner interlocking structures 56, 58 inhibits the rotation, about the central axes CA, CA1, of the liner 14 relative to the shell 12. The mating of the shell and liner interlocking structures 56, 58 and the alignment projection 189 with the alignment recess 36, 136 may occur generally simultaneously. Once the surgeon moves the liner 14 fully into the shell cavity 28, the snap-fit connection will form between liner and the shell to secure the liner in the shell cavity of the shell. The tapered portion 38A of the liner 14 and tapered portion 22A of the shell 12 also create an interference fit to secure the liner in the shell. In fact, the interference fit of the tapered portion due to the difference in angles α and β may secure the liner 14 to the shell 12 even without the snap-fit connection. As the surgeon moves the liner 14 into the shell cavity 28, the lip 54 of the liner is compressed and then expands (e.g., snaps-backs) into the recess 52 of the shell 12, once they become aligned.

With a fixed-bearing implant, such as implant 10, after the liner 14 is coupled to the shell 12, the surgeon then inserts the femoral head 16 (which may already be attached to the stem of the femoral implant) into the liner cavity 42 of the liner. With a dual-mobility implant, such as implant 110, the surgeon will first attach the mobile insert 180 to the femoral head 116 before inserting the mobile insert (and femoral head) into the liner cavity 142 of the liner 114. The femoral head 116 may be attached to the stem of the femoral implant after it is coupled to the mobile insert 180. To attach the mobile insert 180 to the femoral head 116, the surgeon moves the femoral head distally into the mobile insert cavity 186. As the femoral head 116 moves into the mobile insert cavity 186, the femoral head expands the mobile insert 180 (e.g., the proximal end of the mobile insert cavity), which then retracts (e.g., snaps-back) once the femoral head is in the mobile insert cavity. In one embodiment, the surgeon uses a tool or press to couple the mobile insert 180 and the femoral head 116 together. The surgeon then insertions the mobile insert 180, with the femoral head 116, into the liner cavity 142 of the liner 114.

The order of execution or performance of the operations in embodiments of the aspects of the present disclosure described herein are not essential, unless specifically stated or indicated otherwise. That is, the operations may be performed in any order and/or simultaneously, and the embodiments of the aspects of the disclosure may include additional or fewer operations than those disclosed herein. For example, it is contemplated that executing or performing a particular operation before, contemporaneously with, or after another operation is within the scope of the present disclosure.

As is apparent, the implants 10, 110 and elements thereof disclosed herein are generally analogous to one another and, thus, for ease of comprehension, where similar, analogous or identical parts are used between the various different implants (or elements thereof), reference numerals having the same last two digits are employed (and the same subsequent letter, if applicable). For example, shell 12 is analogous to shells 112, 212, 312, 412, 512, and 612 and, thus, all these shells have the same last two digits of "12." Thus, unless clearly stated otherwise, the above descriptions regarding the implants and elements thereof apply equally to all the analogous implants and the elements thereof. For example, at least some of the description related to insertion tool recess 34 may also apply to insertion tool recess 134 and/or vice versa. In another example, at least some of the description related to the inner surface 22 of shell 12 (e.g., the tapered shell section 22A, the spherical shell section 22B and the transition shell section 22C) applies equally to shells 112, 212, 312, 412, 512, 612.

For the materials of each component of dual-mobility application such as one shown in FIG. 17, in one embodiment, the acetabular shell 12 may be made of metal such as a Titanium alloy, liner 14 may be made of either ceramic material or metal such as a cobalt-chrome alloy. For ceramic materials, a preferred material may be Aluminum oxide ($Al_2O_3$). Ceramic material for the liner 14 may be preferred if the fit between the liner and the shell 12 is less than perfect which allows the two materials to rub together. Metal to metal rubbing from micro motion may cause metallic shavings or particles to be dislodged. The mobile insert 180 may be made of polyethylene material such as a compression-molded, GUR 1020E material. The femoral head 160 may be made of metal such as a cobalt-chrome alloy or ceramic material Aluminum oxide ($Al_2O_3$) material.

FIGS. 19A through 24C disclose an impaction tool system for seating an acetabular shell in the acetabular space. When seating the acetabular shell with a conventional impaction tool whose tip is threaded into the central hole 36, there is a possibility that a user may accidentally disengage the tool while orienting the shell in the acetabular space. Thus, it would be desirable to provide an impaction tool that prevents the user from unthreading and disengaging the tool from the shell.

Figure 19A:
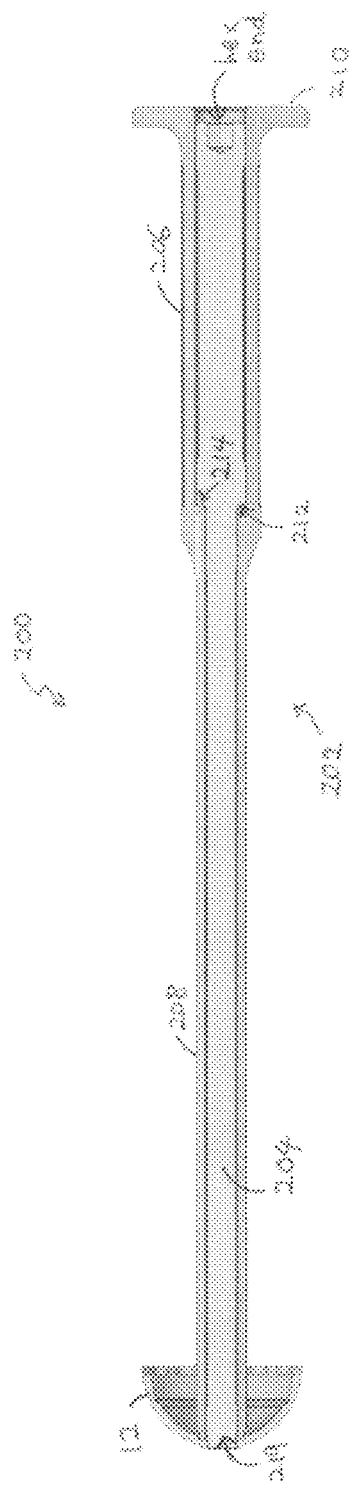
FIGS. 19A and 19B are cross-sectional views of a shell insertion tool according to one aspect the present disclosure.
Figure 19B:
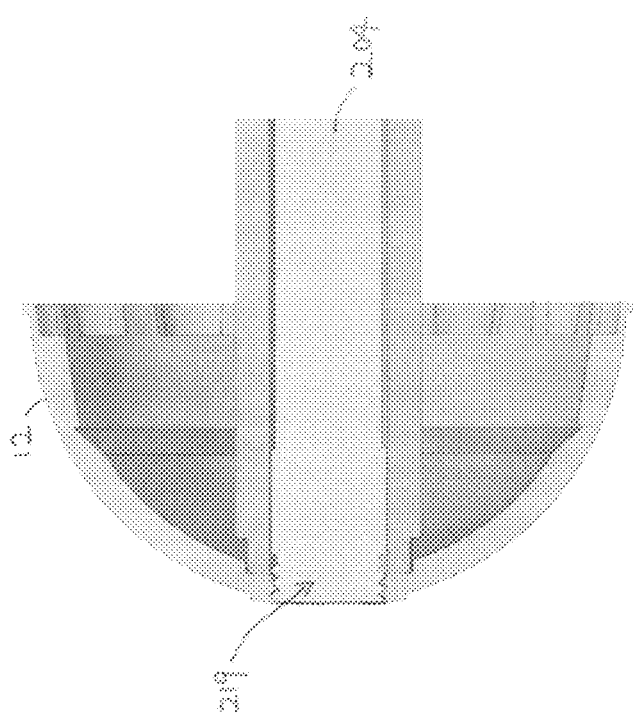

FIGS. 19A and 19B illustrate a shell insertion tool 200 with anti-rotation control according to an embodiment of the present disclosure. The tool 200 has a hollow outer shaft 202 and an internal shaft 204 disposed within the outer shaft. The outer shaft 202 includes a distal sleeve 208, an impactor sleeve 206 extending proximally from a proximal end of the distal sleeve 208. The impactor sleeve 206 includes an impactor head 210. In the embodiment shown, the outer shaft 202 is a single integral piece which is formed from a single metal piece. In other embodiments, the distal sleeve 208 and the impactor sleeve 206 of the outer shaft 202 may be made from two separate pieces that are attached together such as by welding. The impactor sleeve 206 has an internal flat stop 212 which engages a corresponding stop 214 of the internal shaft 204.

Figure 20B:
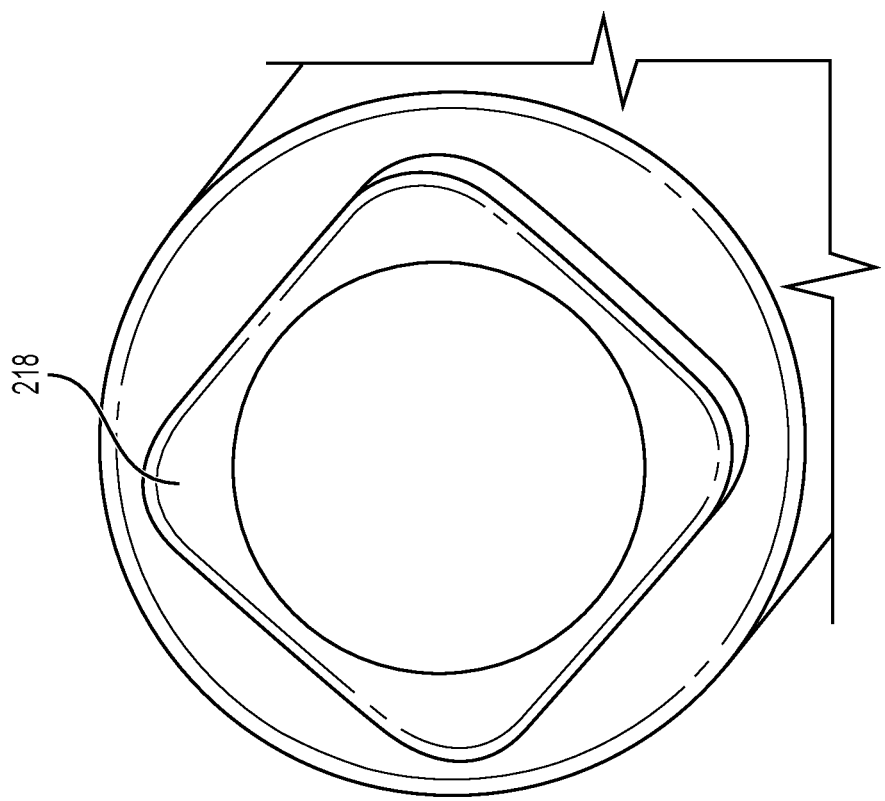
FIGS. 20A and 20B illustrate exemplary anti-rotation projections of the shell insertion tool of FIG. 19 according to one aspect the present disclosure.
Figure 20A:
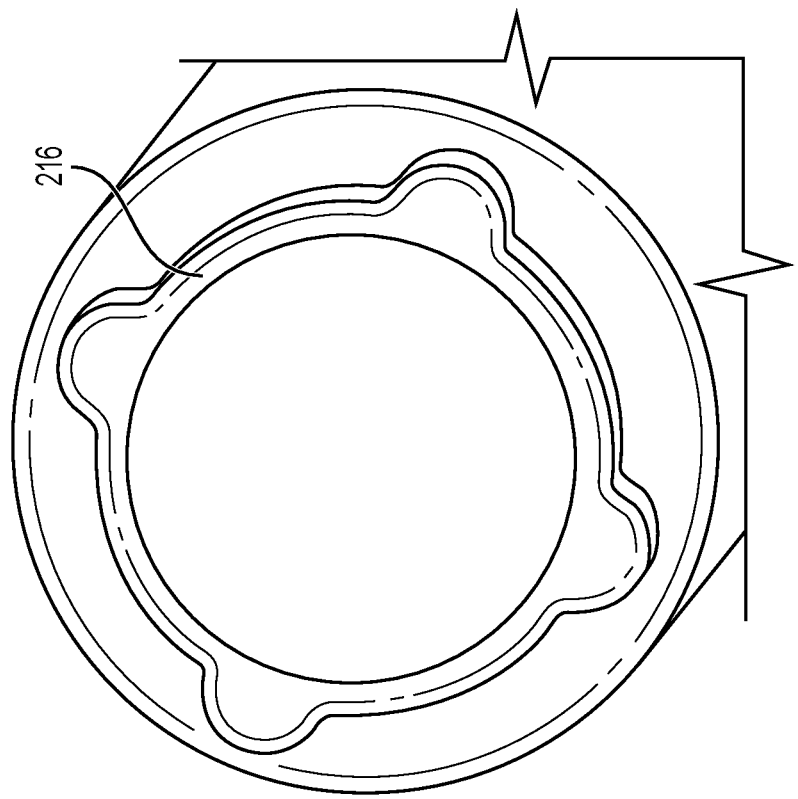

A distal end of the outer shaft 202 as shown in FIGS. 20A and 20B has an anti-rotation projection feature 216,218 in the shape which is complementary to the anti-rotation recess 34, 134, 334 of the acetabular shell 12. For example, FIG. 20A has a round projection 216 and four uniformly spaced semi-circular projections extending laterally from the round projection. The projection 216 of FIG. 20A is configured to be received in the complimentary anti-rotation recess 34 of the acetabular shell 12 as shown in FIG. 4 while the square shaped projection 218 of FIG. 20B is configured to be received in the complimentary anti-rotation recess 334 of the acetabular shell 312 as shown in FIG. 12.

A distal end portion 219 of the internal shaft 204 has an external threading configured to be threaded into internal threading of the central hole 36, as shown for example in FIG. 5. A proximal end portion of the internal shaft 204 has a key feature such as a hex key configured to receive a hex driver for threading the internal shaft 204 into the acetabular shell 12.

This anti-rotation feature of the present design provides rotational stability and is concentric or centered with the threaded central hole of the shell. The new shell inserter instruments can mate with the shell's rotational control feature and thread into the apical/central hole of the shell for insertion and impaction of the acetabular shell. Ultimately, the rotational control feature allows a fully seated positioning of the shell without the potential of unthreading the inserter from the shell.

Figure 21:
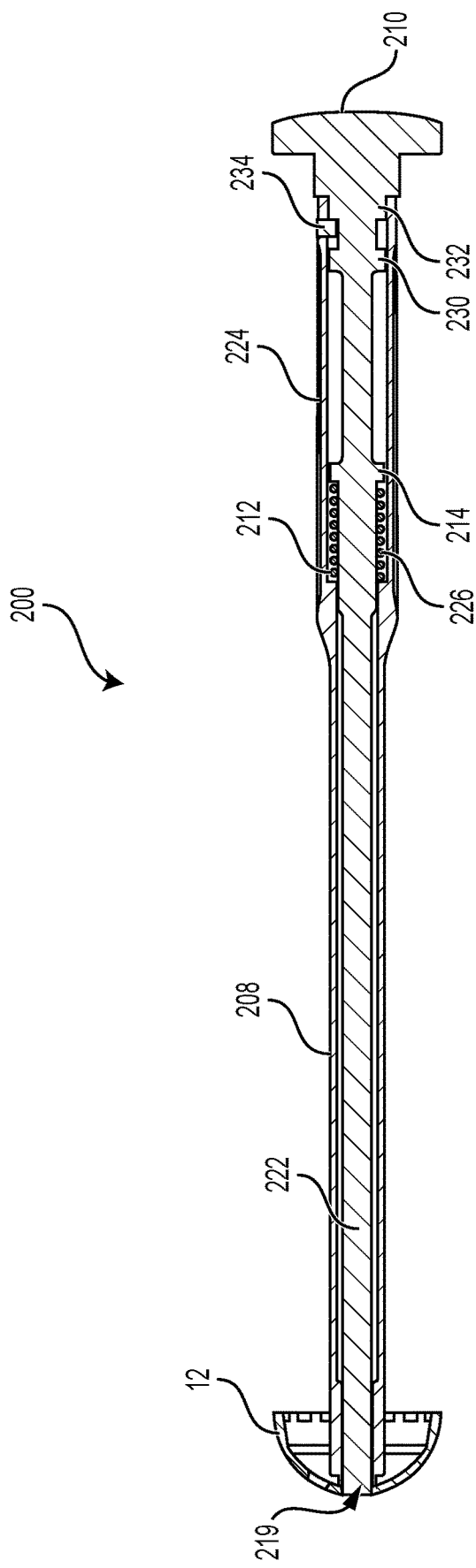
FIG. 21 is a cross-sectional view of a shell insertion tool according to another aspect of the present disclosure.

FIG. 21 illustrates an insertion tool 220 according to another embodiment of the present invention. Unlike the insertion tool 220 of FIG. 19A, the impactor head 210 is part of the internal shaft 222. An annular stop 214 of the internal shaft 222 and a flat stop 212 of the outer shaft 208 captures an internal spring 226 to provide a constant bias of an opposing force at all times. At rest, the insertion tool 220 is in an unthreaded position. The internal shaft 222 is captured in the outer shaft 208 by a pin 234 in an annular recess defined by a stop 230 and 232. The pin 234 is permanently attached to the impactor sleeve 224 by welding, for example. The distal end portion of the internal shaft 222 and outer shaft 208 are the same as those of FIGS. 19A-19B and FIGS. 20A-20B.

Figure 22A:
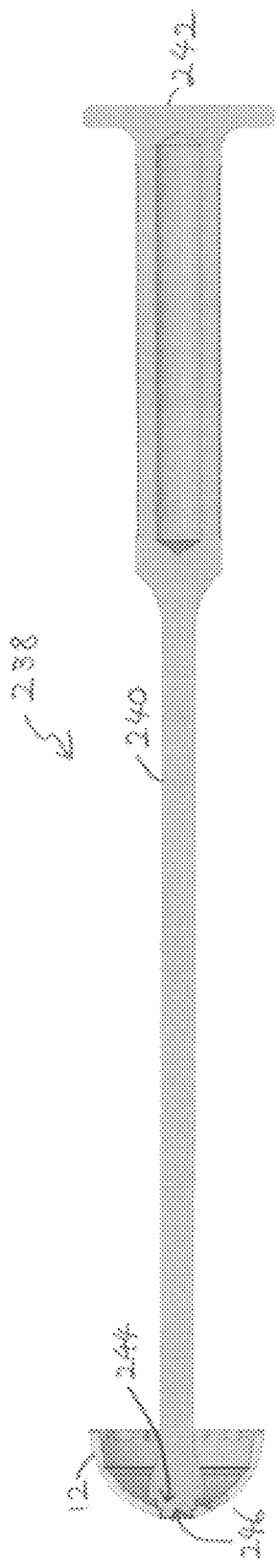
FIGS. 22A and 22B are cross-sectional and perspective views, respectively, of a shell insertion tool according to another aspect the present disclosure.
Figure 22B:
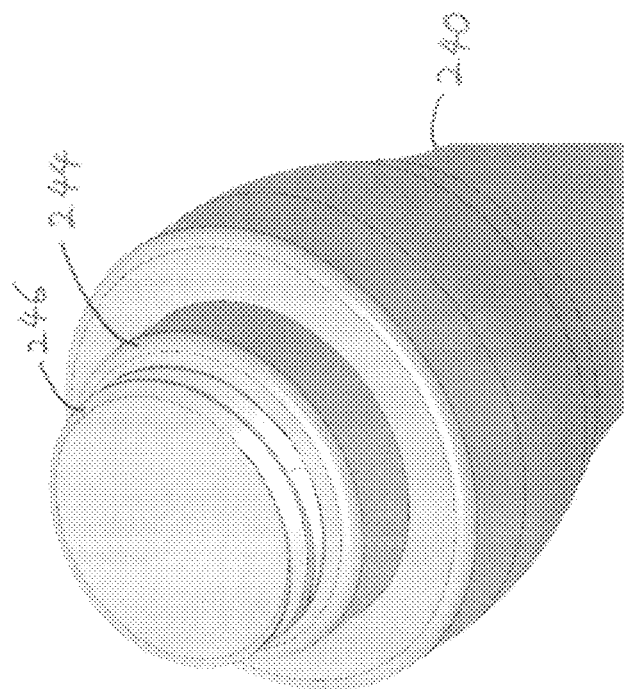

FIGS. 22A and 22B illustrate an insertion tool 238 according to another embodiment of the present invention. Unlike the other insertion tools, the insertion tool 238 is made of a single shaft 240 with an integrated impaction head 242. The shaft 240 includes a distal end portion comprising a distal projection 244 having a lower outer surface designed to sit flush against the surface of the recess 34 without any rotation control and a threaded tip 246 extending distally of the distal projection 244. When the threaded tip 246 is threaded into the threaded central hole 36, the distal projection 244 does not engage the key feature of the recess 34 so that the insertion tool 238 may rotate relative to the acetabular shell 12 about the longitudinal axis of the central hole 36 with perhaps some resistance.

FIG. 23 is a cross-sectional view of a shell insertion tool 200 that attaches to a rim plate according to one aspect of the present disclosure. The use of the rim plate is intended to be an optional secondary step after the initial impaction of the shell 12 into the acetabulum. This rim plate method of impaction allows a greater contact surface area in which the force of impaction spreads out uniformly across the shell's exterior surface. This helps ensures proper seating of the shell 12 into the acetabulum. Although the rim plate impaction method is intended to be an optional secondary step, it may be a primary step without the initial impaction of the shell 12 with the tool 200 locked into the central opening 36 of the shell 12.

The insertion tool 200 of FIG. 23 is identical to that of FIG. 19A, except that it attaches to a rim plate as shown in FIGS. 24A-24C. The rim plates are designed to fit over an upper surface of the acetabular shell. Similar to the acetabular shell, a rim plate 248 of FIG. 24A has a center hole 254 having an internal threading and an anti-rotation recess 256. Similar to the recess of FIG. 20A, the recess 256 has a round projection and four uniformly spaced semi-circular projections extending laterally from the round projection. A rim plate 250 of FIG. 24B has an anti-rotation recess 258 which is square shaped. FIG. 24C is a bottom perspective view of the rim plate 248 of FIG. 24A. Similar to the liner 14 of FIG. 7, the rim plate 248 has uniformly spaced interlocking tabs 260 that rests on corresponding interlocking recesses 60 of the shell 12. In the embodiment shown, there are six tabs 260 that rest on six of the twelve recesses 60 of the shell 12.

Although only the insertion tool 200 is shown in conjunction with the rim plates, any of the insertion tools disclosed herein may be used with any of the rim plates.

All insertion tools as disclosed herein may be provided as part of a complete tool kit.

It is apparent and understood that the elements, features, and/or teachings set forth in each embodiment disclosed herein are not limited to the specific embodiment(s) the elements, features, and/or teachings are described in. Accordingly, it is apparent and understood that the elements, features, and/or teachings described in one embodiment may be applied to one or more of the other embodiments disclosed herein. For example, it is understood that any of the shells disclosed herein may have fastener opening 30 arrangement of shell 12.

Modifications and variations of the disclosed embodiments are possible without departing from the scope of the disclosure defined in the appended claims.

When introducing elements of the present disclosure or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the disclosure, it is intended that all matter contained in the above description and shown in the accompanying drawings shall be interpreted as illustrative and not in a limiting sense.

What is claimed is:

1. An acetabular shell insertion system comprising:
   an acetabular shell including:
      a center hole having an internal threading;
      an anti-rotation recess disposed around the center hole and having a predetermined shape;
   an insertion tool including:
      an outer shaft having an anti-rotation projection shaped to be received in the anti-rotation recess having the predetermined shape so as to prevent rotation of the outer shaft relative to the acetabular shell;
      an inner shaft disposed in the outer shaft and having a threaded tip adapted to be threaded into the internal threading of the center hole to lock the insertion tool to the acetabular shell; and
   a rim plate adapted to rest on the acetabular shell and having a threaded center hole adapted to threadably receive the threaded tip of the insertion tool.

2. The system of claim 1, wherein the anti-rotation recess includes a round recess and a plurality of uniformly spaced cavities extending radially from a central axis of the center hole.

3. The system of claim 1, wherein the anti-rotation recess includes a square-shaped recess.

4. The system of claim 1, further comprising a spring disposed between the outer shaft and the inner shaft to provide a bias to urge the inner shaft proximally away from the center hole of the acetabular shell.

5. The system of claim 4, wherein:
   the outer shaft includes a stop disposed around the inner shaft;
   the inner shaft includes an annular stop disposed inside the outer shaft, the outer shaft stop and the annular stop defining a channel within which the spring is disposed.

6. The system of claim 5, wherein the inner shaft includes an impaction head at its proximal end.

7. The system of claim 1, wherein:
   rim plate includes a plurality of anti-rotation tabs;
   the acetabular shell includes a plurality of anti-rotation recesses that mate with corresponding anti-rotation tabs of the rim plate.

8. The system of claim 1, further comprising a second insertion tool having a single shaft, the single shaft having a threaded tip lacking an anti-rotation projection and adapted to be threaded into the internal threading of the center hole to lock the insertion tool to the acetabular shell, the single shaft further having at its proximal end an impaction head.

9. An acetabular shell insertion tool kit comprising:
   an insertion tool for attaching to an acetabular shell including a center hole having an internal threading and an anti-rotation recess disposed around the center hole and having a predetermined shape, the insertion tool including:
      an outer shaft having an anti-rotation projection shaped to be received in the anti-rotation recess having the predetermined shape so as to prevent rotation of the outer shaft relative to the acetabular shell;
      an inner shaft disposed in the outer shaft and having a threaded tip adapted to be threaded into the internal threading of the center hole to lock the insertion tool to the acetabular shell; and
   a rim plate adapted to rest on the acetabular shell and having a threaded center hole adapted to threadably receive the threaded tip of the insertion tool.

10. The kit of claim 9, wherein the anti-rotation projection includes a round projection and a plurality of uniformly spaced extensions extending radially from a longitudinal axis of the outer shaft.

11. The kit of claim 9, wherein the anti-rotation projection includes a square-shaped projection.

12. The kit of claim 9, wherein the rim plate includes a round recess disposed around the center hole of the rim plate and a plurality of uniformly spaced cavities extending radially from a central axis of the center hole of the rim plate.

13. The kit of claim 9, further comprising a spring disposed between the outer shaft and the inner shaft to provide a bias to urge the inner shaft proximally away from the center hole of the acetabular shell.

14. The kit of claim 13, wherein:
the outer shaft includes a stop disposed around the inner shaft;
the inner shaft includes an annular stop disposed inside the outer shaft, the outer shaft stop and the annular stop defining a channel within which the spring is disposed.

15. The kit of claim 14, wherein the inner shaft includes an impaction head at its proximal end.

16. The kit of claim 9, wherein:
rim plate includes a plurality of anti-rotation tabs that mate with corresponding anti-rotation recesses of the acetabular shell.

17. The kit of claim 9, further comprising a second insertion tool having a single shaft, the single shaft having a threaded tip lacking an anti-rotation projection and adapted to be threaded into the internal threading of the center hole to lock the insertion tool to the acetabular shell, the single shaft further having at its proximal end an impaction head.

18. The kit of claim 9, wherein the rim plate further includes an anti-rotation cavity having the same shape and size as the anti-rotation recess so as to receive the same anti-rotation projection of the insertion tool.

19. The kit of claim 18, wherein the rim plate includes a round recess disposed around the center hole of the rim plate and a plurality of uniformly spaced cavities extending radially from a central axis of the center hole of the rim plate.

* * * * *